(12) United States Patent
Fisher et al.

(10) Patent No.: US 12,070,483 B2
(45) Date of Patent: Aug. 27, 2024

(54) COMPOSITIONS AND METHODS FOR TREATMENT OF ACUTE LUNG INJURY

(71) Applicant: THE TRUSTEES OF THE UNIVERSITY OF PENNSYLVANIA, Philadelphia, PA (US)

(72) Inventors: Aron B. Fisher, Philadelphia, PA (US); Sheldon I. Feinstein, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 783 days.

(21) Appl. No.: 17/269,097

(22) PCT Filed: Aug. 15, 2019

(86) PCT No.: PCT/US2019/046698
§ 371 (c)(1),
(2) Date: Feb. 17, 2021

(87) PCT Pub. No.: WO2020/037146
PCT Pub. Date: Feb. 20, 2020

(65) Prior Publication Data
US 2021/0315964 A1    Oct. 14, 2021

Related U.S. Application Data

(60) Provisional application No. 62/719,217, filed on Aug. 17, 2018.

(51) Int. Cl.
| | | |
|---|---|---|
| *A61K 38/00* | (2006.01) | |
| *A61K 38/08* | (2019.01) | |
| *A61K 38/10* | (2006.01) | |
| *A61P 11/00* | (2006.01) | |

(52) U.S. Cl.
CPC ............. *A61K 38/08* (2013.01); *A61K 38/10* (2013.01); *A61P 11/00* (2018.01)

(58) Field of Classification Search
CPC .......... A61K 38/08; A61K 38/10; A61P 11/00
See application file for complete search history.

(56) References Cited

U.S. PATENT DOCUMENTS

| | | |
|---|---|---|
| 4,861,756 A | 8/1989 | Jackson |
| 2012/0316100 A1 | 12/2012 | Pagano |

FOREIGN PATENT DOCUMENTS

| | | |
|---|---|---|
| RU | 2428979 C2 | 9/2011 |
| WO | 2002006301 A2 | 1/2002 |
| WO | 2020037146 A1 | 2/2020 |

OTHER PUBLICATIONS

International Search Report and Written Opinion, PCT/US2019/046698, dated Jan. 7, 2020.
Raghavendran, et al., "Surfactant Therapy of ALI and ARDS", Grit Care Clin., Jul. 2011, 27(3): 525-559.
Shariat, et al., "Optimization of a Method to Prepare Liposomes Containing HER2/Neu-Derived Peptide as a Vaccine Delivery System for Breast Cancer", Iran J Pharm Res, vol. 13 (Suppl), 2014, pp. 15-25.
European Search Report dated Jun. 1, 2022, EP Application No. 19850140.5.
Benipal, et al., "Inhibition of the phospholipase A2 activity of peroxiredoxin 6 prevents lung damage with exposure to hyperoxia", Redox Biology, vol. 4, Apr. 1, 2015, pp. 321-327, XP055754127, NL ISSN: 2213-2317.
Fisher, et al., "A Peptide Inhibitor of NADPH Oxidase (NOX2) Activation Markedly Decreases Mouse Lung Injury and Mortality Following Administration of Lipopolysaccharide (LPS)", International Journal of Molecular Sciences, vol. 20, No. 10, May 15, 2019, p. 2395, XP055921765, Basel, CH ISSN: 1661-6596.
Krishnaiah, et al., "Binding sites for interaction of peroxiredoxin 6 with surfactant protein A", Biochimica et Biophysica Acta (BBA)—Proteins & Proteomics, Elsevier, Netherlands, vol. 1864, No. 4, Dec. 23, 2015, pp. 419-425, XP029428504, ISSN: 1570-9639.
Fisher, et al., "Identification of Small Peptides that Inhibit NADPH Oxidase (Nox2) Activation," Antioxidants, Dec. 5, 2018, 7, 181, pp. 1-13.
Lee, et al., "A Novel Nontoxic Inhibitor of the Activation of NADPH Oxidase Reduces Reactive Oxygen Species Production in Mouse Lung", Journal of Pharmacology and Experimental Therapeutics, 2013, vol. 345(2), pp. 284-296.

*Primary Examiner* — Jeanette M Lieb
(74) *Attorney, Agent, or Firm* — Saul Ewing LLP; Kathryn Doyle; Justin Crotty

(57) ABSTRACT

In various aspects and embodiments the invention provides compositions and methods useful in the treatment of acute lung injury (ALI).

19 Claims, 17 Drawing Sheets
Specification includes a Sequence Listing.

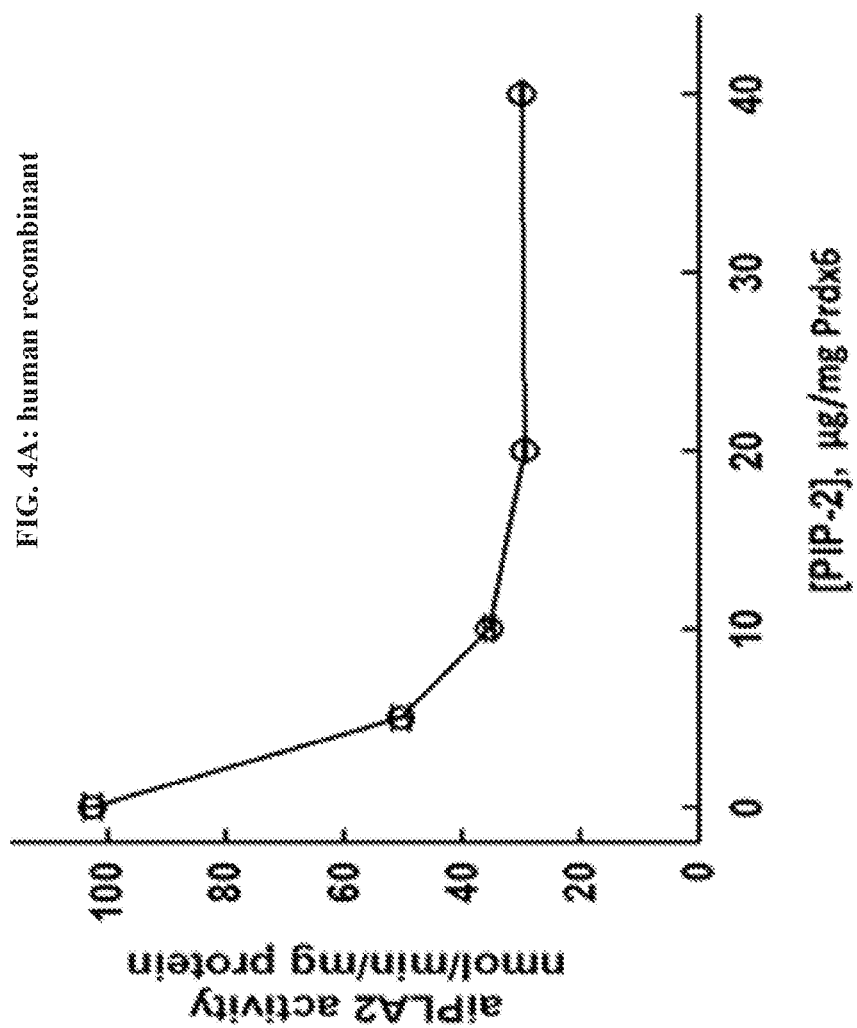

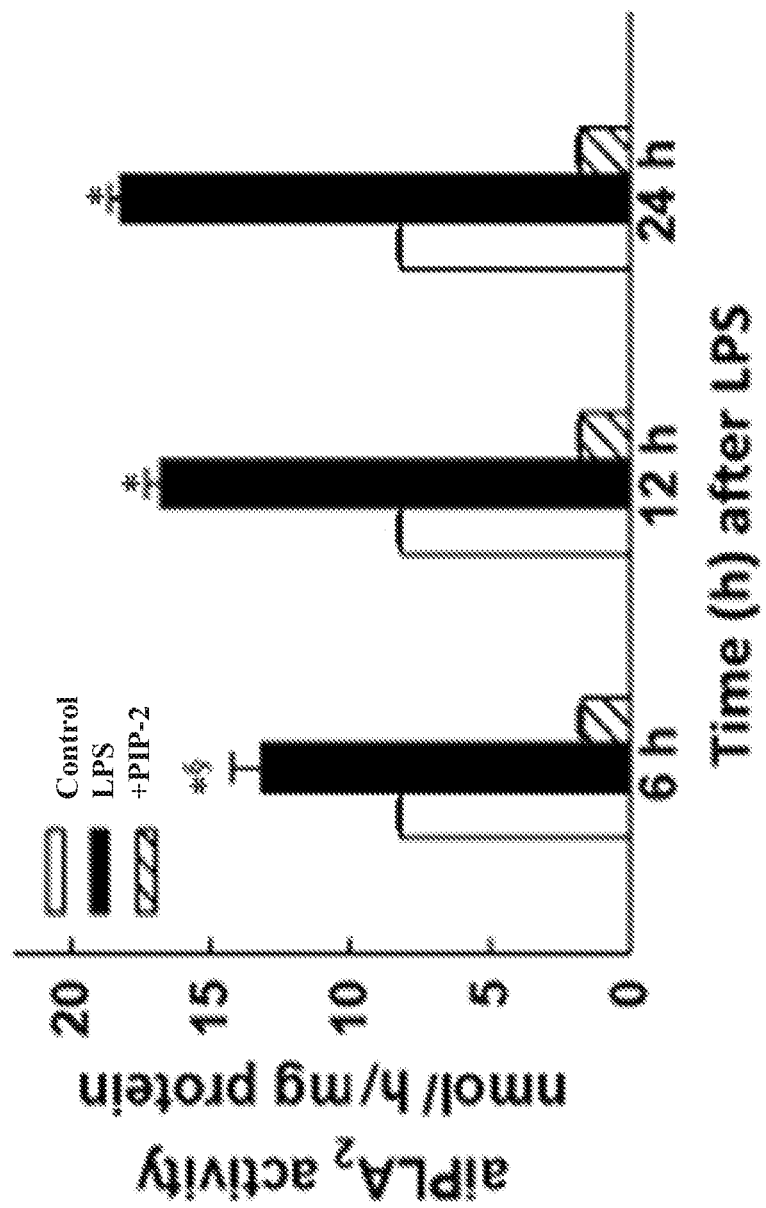
FIG. 4B: mouse lung

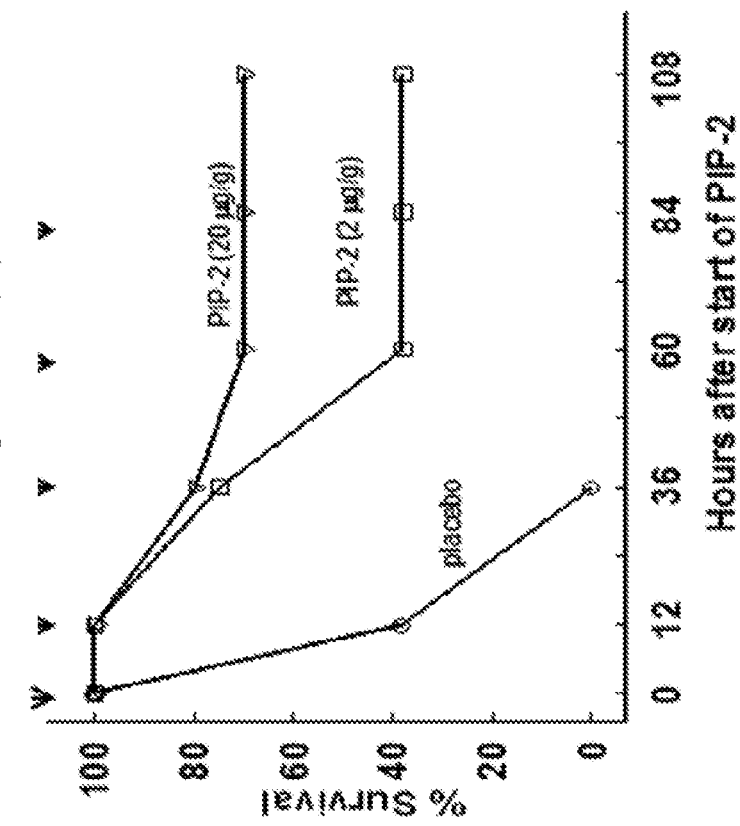
FIG. 7B: Intraperitoneal (IP) LPS
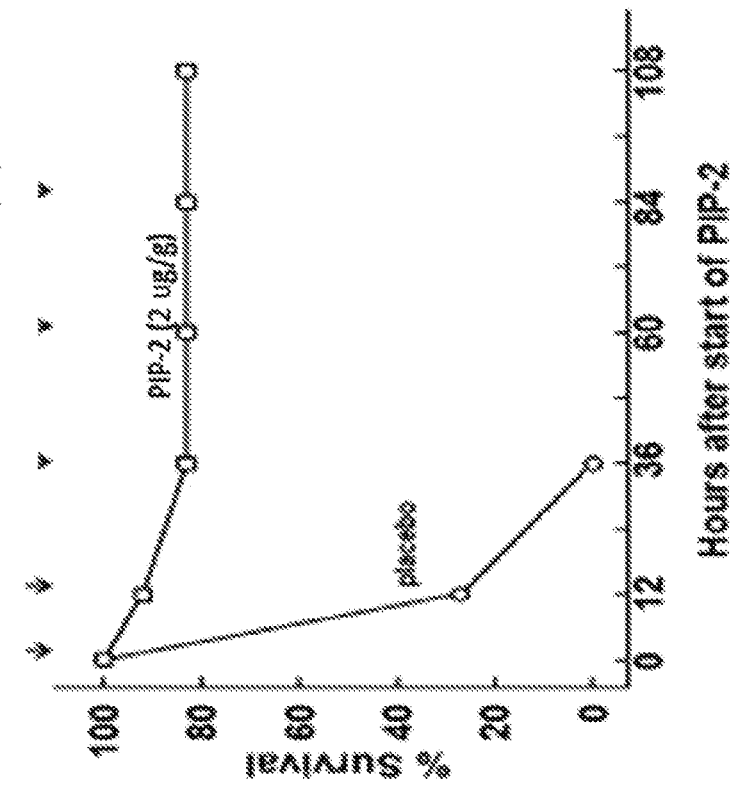
FIG. 7A: Intratracheal (IT) LPS

| Composition* % DPPC/PC/PG | PIP-2 | n | Activity[1] nmol/mg prot/h | Inhibition % | % max. inhibition |
|---|---|---|---|---|---|
| 50/25/10 | no | 2 | 8.83 ± 0.1 | ---- | ---- |
| 50/25/10 | yes | 3 | 1.64 ± 0.04 | 81.4 | 100 |
| 0/75/10 | yes | 3 | 1.72 ± 0.06 | 80.5 | 99 |
| 75/0/10 | yes | 2 | 1.84 ± 0.02 | 79.2 | 97 |
| 55/30/0 | yes | 2 | 2.50 ± 0.12 | 71.7 | 88 |

FIG. 10

| Condition | # of cells in BALF (x10^4/g body wt) | Total protein in BALF (µg/g body wt) | Wet/Dry weight of lung | TBARS pmol/mg prot. | 8-isoprostanes pmol/mg prot | Protein carbonyls nmol/mg prot |
|---|---|---|---|---|---|---|
| % Protection by PIP-2 @ 0/12/16 h* | 100/44/94* | 100/90/93* | 100/86/76* | 100/97/95* | 100/94/91* | 100/93/93* |

FIG. 11

| | BALF Cells ×10⁴/g Body wt. | BALF Protein µg/g wt. | Wet/Dry Ratio | TBARS pmol/mg prot | 8-Isoprostanes pmol/mg prot | Protein Carbonyls nmol/mg prot |
|---|---|---|---|---|---|---|
| A. Control (no LPS) | 0.95 ± 0.04 | 75 ± 1.3 | 5.59 ± 0.03 | 75 ± 6 | 34 ± 3 | 5.60 ± 0.20 |
| B. LPS (IT) + PIP-2 (2 µg/g body wt) | 0.96 ± 0.04 | 78 ± 2.2 | 5.34 ± 0.03 | 77 ± 1 | 34 ± 3 | 5.60 ± 0.20 |
| C. LPS (IP) + PIP-2 (20 µg/g body wt) | 0.95 ± 0.05 | 79 ± 2.0 | | 77 ± 2 | 35 ± 1 | 5.52 ± 0.14 |

FIG. 12

| | # of cells in BALf (x10^4/g body wt) | Total Protein in BALf (μg/g body wt) | Wet/Dry weight ratio of lung | TBARS pmol/mg prot. | 8-Isoprostanes pmol/mg prot | Protein carbonyls nmol/mg prot |
|---|---|---|---|---|---|---|
| Control | 0.97 ± 0.06 | 77 ± 2.0 | 5.61 ± 0.02 | 74.6 ± 2.3 | 33.1 ± 3.0 | 5.6 ± 0.2 |
| VILI | 19.6 ± 1.4 | 235 ± 10 | 10.82 ± 0.21 | 530 ± 7 | 174 ± 5 | 22.8 ± 0.8 |
| VILI + PIP-2 | 8.4 ± 0.3* | 107 ± 8* | 7.42 ± 0.11* | 210 ± 4* | 77.4 ± 1.0* | 8.6 ± 0.4* |
| % Protection | 60 | 81 | 65 | 70 | 69 | 83 |

FIG. 13

COMPOSITIONS AND METHODS FOR TREATMENT OF ACUTE LUNG INJURY

CROSS REFERENCE TO RELATED APPLICATIONS

The present application is a 35 U.S.C. § 371 national phase application from, and claims priority to, International Application No. PCT/US2019/046698, filed Aug. 15, 2019, and published under PCT Article 21(2) in English, which is entitled to priority under 35 U.S.C. § 119(e) to U.S. Provisional Patent Application No. 62/719,217, filed Aug. 17, 2018, which are hereby incorporated by reference in their entireties herein.

STATEMENT REGARDING FEDERALLY SPONSORED RESEARCH OR DEVELOPMENT

This invention was made with government support under HL102016 and HL075587 awarded by the National Institutes of Health. The government has certain rights in the invention.

BACKGROUND OF THE INVENTION

Lung inflammation is an important component in the pathogenesis of the acute lung injury (ALI) syndrome that results from diverse etiologies. Lung inflammation associated with the production of reactive oxygen species (ROS) is an important contributor to the ALI syndrome. Activation of NADPH oxidase, type 2 (NOX2), the major source of ROS in lungs, requires the phospholipase $A_2$ ($PLA_2$) activity of peroxiredoxin 6 (Prdx6).

Current treatment of ALI is supportive and there is no currently approved drug specifically for its prevention or treatment. Therefore, there is a need in the art for methods and compositions that protect against ALI. The present disclosure addresses this need.

SUMMARY OF THE INVENTION

In one aspect, the invention provides a composition comprising a polypeptide consisting of:

$$X^1X^2X^3X^4X^5LX^6X^7X^8X^9HQIL \qquad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be present or absent and if present is T or E;
$X^6$ is H or Y;
$X^7$ is D or E;
$X^8$ is F or I; and
$X^9$ is R or K.

In various embodiments, the polypeptide is selected from the group consisting of: SEQ ID NO: 5 ELQTELYEIKHQIL, SEQ ID NO: 6 QTELYEIKHQIL and SEQ ID NO: 7 ELYEIKHQIL.

In various embodiments, the polypeptide is selected from the group consisting of: SEQ ID NO: 1 LHDFRHQIL, SEQ ID NO: 2 LYEIKHQIL or SEQ ID NO: 3 LYDIRHQIL.

In various embodiments, the composition further comprises a pharmaceutically acceptable carrier.

In various embodiments, the polypeptide is encapsulated in one or more liposomes.

In various embodiments, the composition is formulated for aerosol inhalation or intratracheal or intravenous injection. In various embodiments, the pharmaceutical composition is administered to the subject by intravenous injection.

In another aspect, the invention provides a method of treating acute lung injury in a subject, the method comprising administering to the subject an effective amount of a pharmaceutical composition comprising a polypeptide consisting of:

$$X^1X^2X^3X^4X^5LX^6X^7X^8X^9HQIL \qquad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be T or E;
$X^6$ is H or Y;
$X^7$ is D or E;
$X^8$ is F or I; and
$X^9$ is R or K.
and a pharmaceutically acceptable carrier.

In various embodiments, the polypeptide is selected from the group consisting of: SEQ ID NO: 5 ELQTELYEIKHQIL, SEQ ID NO: 6 QTELYEIKHQIL and SEQ ID NO: 7 ELYEIKHQIL.

In various embodiments, the polypeptide is selected from the group consisting of: SEQ ID NO: 1 LHDFRHQIL, SEQ ID NO: 2 LYEIKHQIL or SEQ ID NO: 3 LYDIRHQIL.

In various embodiments, the polypeptide is encapsulated in one or more liposomes.

In various embodiments, the pharmaceutical composition is administered to the subject by aerosol inhalation or by intratracheal or intravenous injection.

In another aspect, the invention provides a method of treating sepsis in a subject, the method comprising administering to the subject an effective amount of a pharmaceutical composition comprising a polypeptide consisting of:

$$X^1X^2X^3X^4X^5LX^6X^7X^8X^9HQIL \qquad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be T or E;
$X^6$ is H or Y;
$X^7$ is D or E;
$X^8$ is F or I; and
$X^9$ is R or K.
and a pharmaceutically acceptable carrier.

In various embodiments, the polypeptide is selected from the group consisting of: SEQ ID NO: 5 ELQTELYEIKHQIL, SEQ ID NO: 6 QTELYEIKHQIL and SEQ ID NO: 7 ELYEIKHQIL In various embodiments, the polypeptide is selected from the group consisting of: SEQ ID NO: 1 LHDFRHQIL, SEQ ID NO: 2 LYEIKHQIL or SEQ ID NO: 3 LYDIRHQIL.

In various embodiments, the polypeptide is encapsulated in one or more liposomes.

In various embodiments, the pharmaceutical composition is administered to the subject by aerosol inhalation or by intratracheal or intravenous injection. In various embodiments, the pharmaceutical composition is administered to the subject by intravenous injection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts thiobarbituric acid reactive substances (TBARS). FIG. 2B depicts 8-isoprostanes. FIG. 2C depicts protein carbonyls in the lung homogenate. FIG. 2D depicts the number of cells in bronchoalveolar lavage fluid (BALF). FIG. 2E depicts total protein in BALF. FIG. 2F depicts the ratio of wet to dry weight of the lung.

FIG. 3A depicts the number of cells in BALF. FIG. 3B depicts total protein in BALF. FIG. 3C depicts the ratio of wet to dry weight of lung. FIG. 3D depicts TBARS. FIG. 3E depicts 8-isoprostanes. FIG. 3F depicts protein carbonyls in the lung homogenate.

FIGS. 4A and 4B: Phospholipase $A_2$ of Prdx6 (aiPLA$_2$) was measured by the liberation of palmitic acid from dipalmitoylphosphatidylcholine under acidic conditions (pH 4) in the absence of $Ca^{2+}$. FIG. 4A: The effect of increasing concentration of PIP-2 on the aiPLA$_2$ activity of recombinant human Prdx6. FIG. 4B: The effect of LPS and PIP-2 treatment on aiPLA$_2$ activity of mouse lungs. Mice (n=3 for each condition) were treated with intratracheal LPS (2 µg/g body wt) without or with PIP-2 (2 µg/g body weight) in liposomes. Animals were sacrificed at 6,12, or 24 h after receiving LPS. Lungs were cleared of blood and homogenized. Control lungs were from mice that did not receive LPS. *$P<0.05$ vs corresponding control and vs LPS+PIP-2; § $P<0.05$ vs LPS at 12 and 24 h.

FIG. 5A: Isolated lungs were perfused in a recirculating system with artificial medium. NOX2 activity was stimulated by addition of angiotensin II (Ang II). Amplex red along with horseradish peroxidase were added to the perfusate for detection of ROS production. Aliquots of perfusate were analyzed at intervals by spectrophotometry to determine oxidation of amplex red, indicating ROS production. Results are mean±SE for N=3-4. FIG. 5B: Mice were sacrificed at 6, 12, or 24 h after LPS administration (5 mg/g body wt) and lungs were perfused in situ for 15 min with saline solution containing a fluorophore (difluorofluorescein diacetate, DFFDA). Lungs then were homogenized and fluorescence of the lung homogenate was determined as an index of ROS production. Results for FIG. 5A & FIG. 5B are mean±SE for N=4. *$P<0.05$ vs corresponding LPS and LPS+PIP-2; § $P<0.05$ vs 12 h and 24 h LPS; $\Delta P<0.05$ vs corresponding LPS.

FIGS. 7A and 7B: Kaplan-Meier plots for survival. LPS (15 mg/g body wt) was given to all mice either by: FIG. 7A: intratracheal (IT) or FIG. 7B: intraperitoneal (IP) injection. PIP-2 in liposomes or placebo (liposomes alone) was administered intravenously (IV) 12 h after LPS (this is treatment time zero) and then at 12 or 24 h intervals for a total of 5 doses as indicated by the arrows. FIG. 7A: PIP-2 at 2 µg/g body wt; N=14 for each group. FIG. 7B: PIP-2 at 2 or 20 µg/g body wt.; Placebo group, n=8; PIP-2 2 mg group, n=7; PIP-2 20 mg group, n=10.

FIGS. 9A and 9B: PIP-2 inhibits the increased lung aiPLA2 activity and increased ROS generation after LPS administration. LPS (5 µg/g body weight) was administered by intratracheal (IT) instillation along with liposomes alone (labeled as LPS) or with PIP-2 in liposomes (labeled as +PIP-2). Control was liposomes alone without LPS (labeled as control). Mice were sacrificed at 6, 12, or 24 h after LPS and lungs were perfused in situ for 15 min with saline solution containing the fluorophore difluorofluoroscein diacetate (DFF-DA). Lungs then were homogenized and assayed for: FIG. 9A: aiPLA2 activity; FIG. 9B: fluorescence of the lung homogenate as an index of ROS production. Results are mean±SE for N=3 for A and N=4 for B. *P<0.05 vs. Control and +PIP-2 at the same time point; ΔP<0.05 vs. corresponding value at 6 h.

FIG. 10: Effect of liposome composition on delivery of PIP-2 to lungs after IV administration. Same protocol for liposome-mediated delivery of PIP-2 by intravenous infusion as for FIGS. 5A-5B. * % of total lipid; all liposomes also contained 15% cholesterol. † Mean±SE for n=3 or range for n=2. PC or DPPC within liposomes have similar effectiveness for intracellular delivery of PIP-2. Omission of PG results in ~10% decrease in efficacy.

FIG. 11: "Protection" (%) by PIP-2 against lung injury evaluated at 24 hr after IT LPS. *Values for PIP-2 effect with administration at 0, 12, or 16 h after LPS. Protection (%) against lung injury was calculated as [1−(injury with PIP-2−control)/(LPS alone−control)]. "Protection" by PIP-2 is >75%.

FIG. 12: Indices of lung injury in PIP-2 treated mice that survive high dose LPS. Mice were injected with LPS (15 µg/g wt) either: Line B. intratracheally (IT); or Line C. intraperitoneally (IP). PIP-2 at 2 µg/g or 20 µg/g body wt in liposomes was injected (IV) at the times indicated in FIG. 7. Five of the surviving mice were sacrificed at 108 h after the start of treatment (120 h after LPS administration). Results are compared to values for historical control mice (no LPS) (Line A). BALf, bronchoalveolar lavage fluid; TBARS, thiobarbituric reactive substances. Values are mean±SE for n=4 for control and n=5 for LPS+PIP-2. None of the mean values for LPS+PIP-2 are statistically different (p>0.05) from the corresponding control. PIP-2 treated mice that survive 5 days after LPS had normal lungs.

FIG. 13: Effect of PIP-2 on ventilation-induced lung injury (VILI). Anesthetized mice were mechanically ventilated for 6 h with tidal volume 12 ml/Kg body weight with a respiratory rate 120/min, and 2 cm $H_2O$ positive end-expiratory pressure (PEEP). PIP-2 (2 ug/g body wt) in liposomes was administered by IT injection at the start of mechanical ventilation and mice were sacrificed 6 h later. Control represents values for normal (non-ventilated) lungs. % Protection was calculated as in Table 1. Results are mean±SE for n=4. *P<0.05 for VILI+PIP vs VILI. PIP-2 protected against lung injury associated with mechanical ventilation.

DETAILED DESCRIPTION

Definitions

Figure 1A:
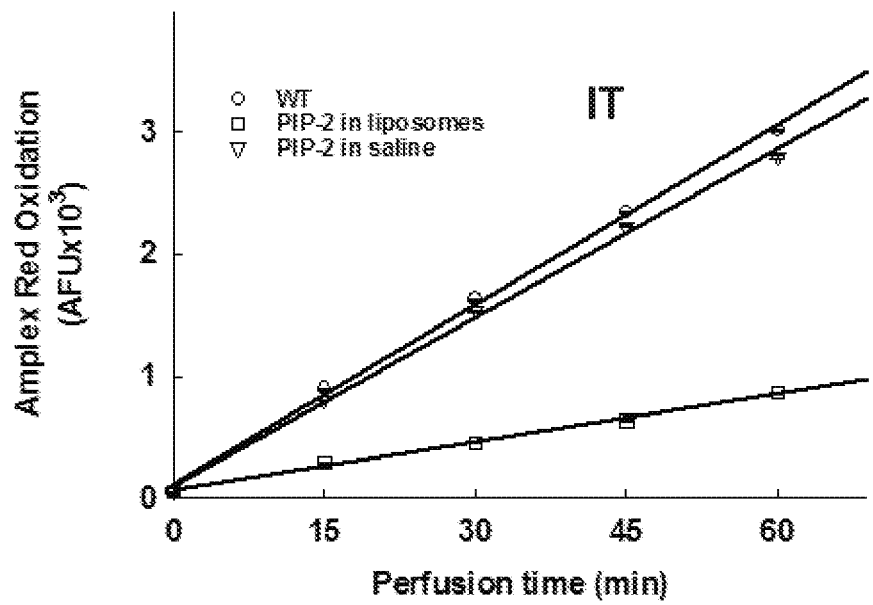
FIGS. 1A and 1B: Wild type C57Bl/6 mice at age 8-10 weeks were injected with 2 ug/g body wt of PIP-2 either through an intratracheal catheter (IT) or intravenously (IV). The injected peptide was dissolved in saline or was incorporated into unilamellar liposomes consisting of dipalmitoyl phosphatidylcholine (DPPC), egg phosphatidylcholine (PC), phosphatidylglycerol (PG), and cholesterol (molar ratio of lipids, 50:25:10:15). We have determined that liposomes containing either 75% DPPC or 75% egg PC (plus PG and cholesterol) are equally effective to the DPPC/PC/PG/cholesterol liposomes for intracellular delivery of PIP-2. Mice were sacrificed after 5 min, lungs were perfused until cleared of blood, and then subjected to recirculating perfusion under temperature-controlled (37° C.) conditions in the presence of the fluorescent indicator Amplex red plus horseradish peroxidase (HRP) in order to monitor the oxidation of Amplex red by $H_2O_2$. The fluorescence of aliquots of perfusate was measured at the indicated times and expressed as arbitrary fluorescence units (AFU). The increasing fluorescence with time of perfusion indicates the production of $H_2O_2$ reflecting the activation of cellular NADPH oxidase (NOX2). Administration of PIP-2 in saline has no effect on the rate of $H_2O_2$ production but PIP-2 in liposomes injected either IT (FIG. 1A) or IV (FIG. 1B) markedly inhibits generation of $H_2O_2$.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Acute lung injury" or "ALP" as used herein refer to a syndrome characterized by acute onset of bilateral pulmonary infiltrates with hypoxemia that is not associated with heart failure.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, "PIP-2" means a peptide having
SEQ ID NO: 1
LHDFRHQIL.

As used herein, "PIP-4" means a peptide having
SEQ ID NO: 2
LYEIKHQIL.

As used herein, "PIP-5" means a peptide having
SEQ ID NO: 3
LYDIRHQIL.

As used herein, "treating a disease or disorder" means reducing the frequency with which a symptom of the disease or disorder is experienced by a patient. Disease and disorder are used interchangeably herein.

As used herein, "sepsis" is a potentially life-threatening condition caused by the body's response to an infection and can lead to multiple organ failure.

As used herein, the term "treatment" or "treating" encompasses prophylaxis and/or therapy. Accordingly the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Compositions

The invention is based in part on the engineering of specific peptide inhibitors of aiPLA$_2$ that may be used to treat ALI. The aiPLA$_2$ inhibiting activity of several peptides of the invention is shown below in Table 1

TABLE 1

Effect of peptides on aiPLA2 activity of recombinant hPrdx6

| sequence | Activity nmol/min/ mg prot. |
|---|---|
| SEQ ID NO: 8 DEELQATLHDFRHQIL (16) human PIP-1 | 45.0 |
| SEQ ID NO: 9 DEELQTELYEIKHQIL (16) rat, mouse PIP-3 | 32.0 |
| SEQ ID NO: 10 ELQTELYEIKHQIL (14) | 33.2 |
| SEQ ID NO: 11 QTELYEIKHQIL (12) | 31.5 |
| SEQ ID NO: 12 ELYEIKHQIL (10) | 28.6 |
| SEQ ID NO: 13 YEIKHQIL (8) | 94.4 |
| SEQ ID NO: 14 IKHQIL (6) | 97.1 |
| SEQ ID NO: 15 DEELQTELYEIKHQ (14) | 102 |
| SEQ ID NO: 16 DEELQTELYEIK (12) | 95.7 |
| SEQ ID NO: 17 DEELQTELYEI (10) | 94.9 |
| SEQ ID NO: 18 DEELQTEL (8) | 93.6 |
| hPrdx6 only (no peptide) | 93.4 |
| SEQ ID NO: 9 DEELQTELYEIKHQIL (16) r | 20.1 |

TABLE 2

Size optimization of inhibitory peptide by effect on aiPLA₂ activity of human recombinant protein

| sequence | Activity nmol/min/ mg prot. |
|---|---|
| SEQ ID NO: 19 TLHDFRHQIL (10) | 31.5 |
| SEQ ID NO: 1 LHDFRHQIL (9) PIP-2 | 29.9 |
| SEQ ID NO: 20 TLHDFRHQI (9) | 89.6 |
| SEQ ID NO: 21 LHDFRHQI (8) | 93.6 |
| SEQ ID NO: 2 LYEIKHQIL (9) PIP-4 | 32.3 |
| SEQ ID NO: 22 ELYEIKHQI (9) | 93.5 |
| SEQ ID NO: 23 LYEIKHQI (8) | 92.1 |
| hPrdx6 only | 92.0 |
| SEQ ID NO: 9 DEELQTELYEIKHQIL (16) r | 32.0 |

TABLE 3

Substitutions in PIP-2: effect on inhibition of aiPLA2 activity of human recombinant Prdx6

| sample | sequence | Activity nmol/min/ mg prot. |
|---|---|---|
| SN019 | SEQ ID NO: 24 LKIEYHQIL | 97.67 |
| SN020 | SEQ ID NO: 25 LRFDHHQIL | 98.97 |
| SN021 | SEQ ID NO: 3 LYDIRHQIL-PIP-5 | 29.74 |
| SN022 | SEQ ID NO: 26 LHEFKHQIL | 99.42 |
| SN023 | SEQ ID NO: 27 LFKLEHQIL | 97.95 |
| SN024 | SEQ ID NO: 28 LHDFRDQIL | 102.04 |
| SN025 | SEQ ID NO: 29 LHDFRPQIL | 101.34 |
| SN026 | SEQ ID NO: 30 LHDFRHNIL | 98.97 |
| SN029 | SEQ ID NO: 31 LHDFRHIIL | 97.30 |
| SN028 | SEQ ID NO: 32 LHDFRHQLL | 102.45 |
| SN029 | SEQ ID NO: 33 LHDFRHQTL | 100.35 |
| No peptide | hPrdx6 only | 99.91 |
| PIP-2* (PIP-4)* *naturally occurring | SEQ ID NO: 1 LHDFRHQIL (SEQ ID NO: 2 LYEIKHQIL) | 26.18 Not tested |

Accordingly, in one aspect, the invention provides a composition comprising a polypeptide consisting of:

$$X^1X^2X^3X^4X^5LX^6X^7X^8X^9HQIL \quad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be present or absent and if present is T or E;
$X^6$ is H or Y;
$X^7$ is D or E;
$X^8$ is F or I; and
$X^9$ is R or K.

Figure 1B:
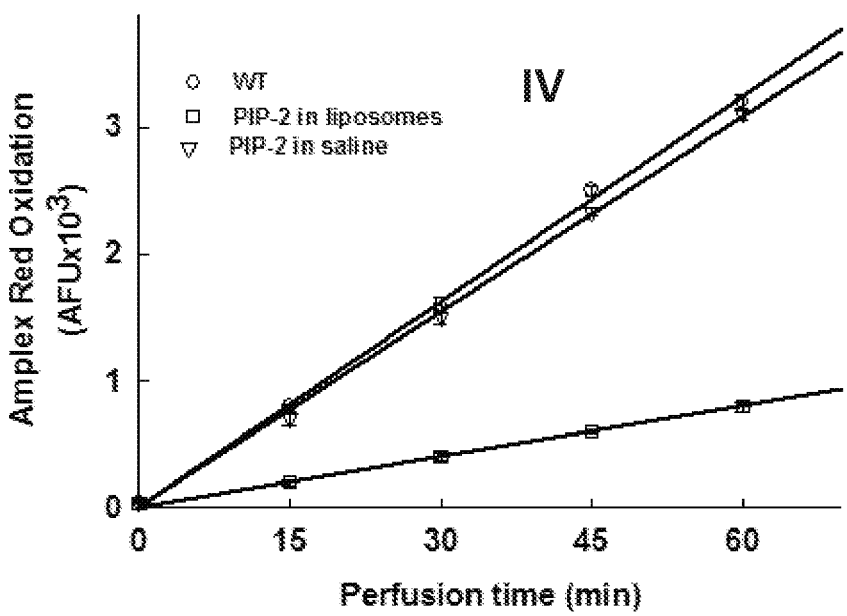
Figure 2C:
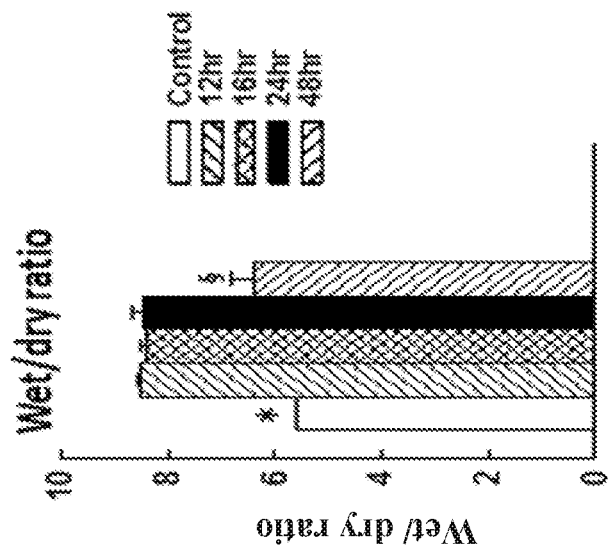
FIGS. 2A-2F depict a time course of lung injury after intratracheal injection of lipopolysaccharide (LPS) by following various markers of tissue oxidation and lung inflammation. Bacterial (E. coli) lipopolysaccharide (LPS) was administered to wild type C57Bl/6 mice by intratracheal (IT) injection at 5 ug/g body wt. Mice were sacrificed at 12,16, 24, or 48 h after LPS as indicated. Lungs were removed and lavaged with saline through the trachea to obtain the BALf; the lung was then homogenized. Parameters of lung injury were nucleated cells and protein in the BALf and the ratio of lung wet to dry weight (W/D); for W/D, the weight of the left upper lobe of the lung was measured before and after drying to constant weight in an oven. Indices of tissue oxidative stress (lower row) were thiobarbituric acid reactive substances (TBARS), 8-isoprostanes, and protein carbonyls measured in the lung homogenate. Values are mean±for n=4. *$P<0.05$ vs all other values; § $p<0.05$ vs 12 h, 16 h and 24 h.
Figure 2B:
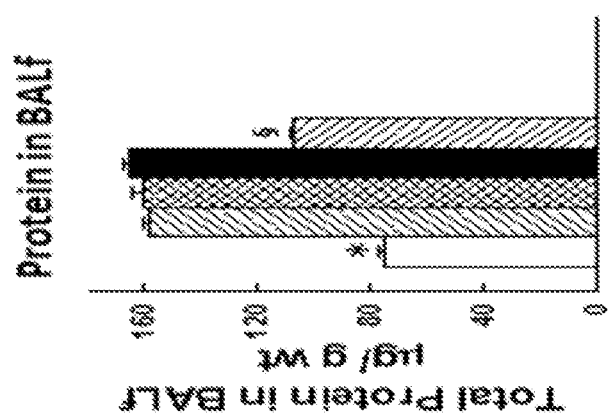
Figure 2A:
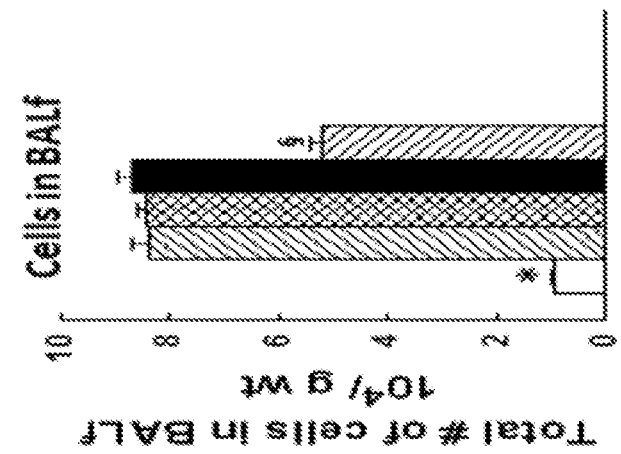
Figures 2D, 2E, 2F:
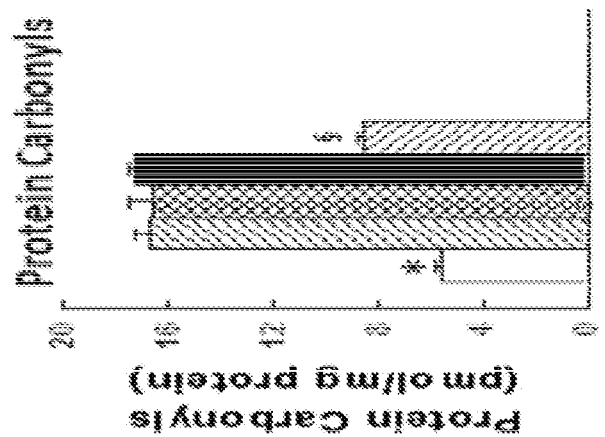
Figure 3A:
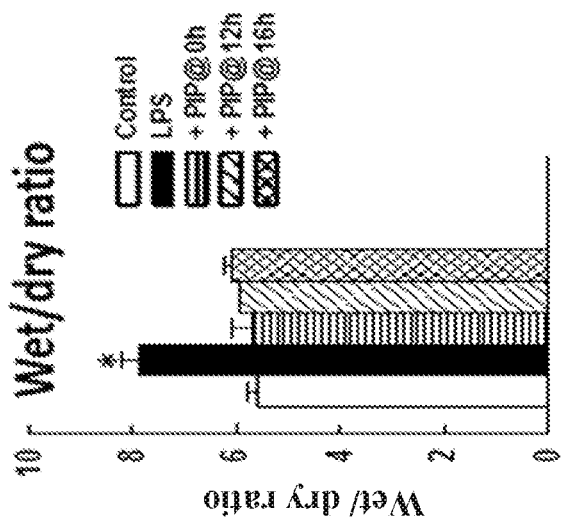
FIGS. 3A-3F Acute lung injury (ALI) was produced with intratracheal LPS (5 mg/g body wt). PIP-2 (2 µg/g body wt) in liposomes was administered IT along with LPS (0 h) or intravenously (IV) at 12 or 16 h after LPS. PIP-2 was administered IV to avoid a second 'assault' on the trachea. Mice were sacrificed at 24 h and lungs were evaluated for lung injury and tissue oxidative stress. Results are mean+SE for n=4. *$P<0.05$ vs all other groups.
Figure 3B:
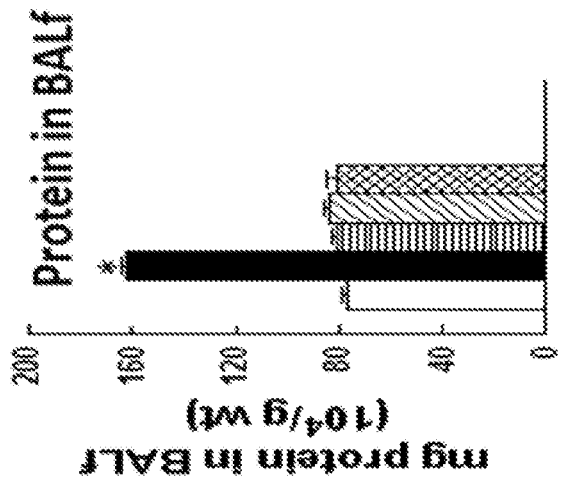
Figure 3C:
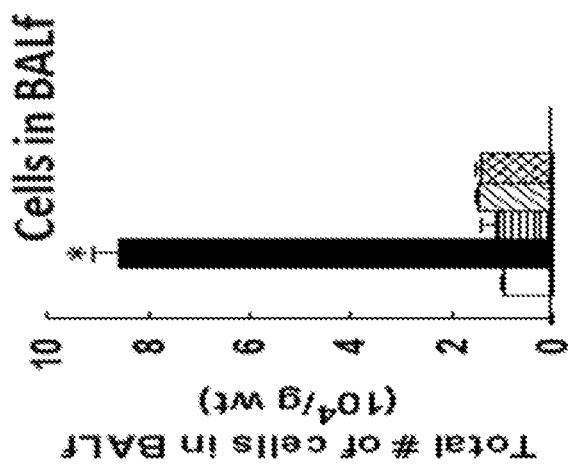
Figures 3D, 3E, 3F:
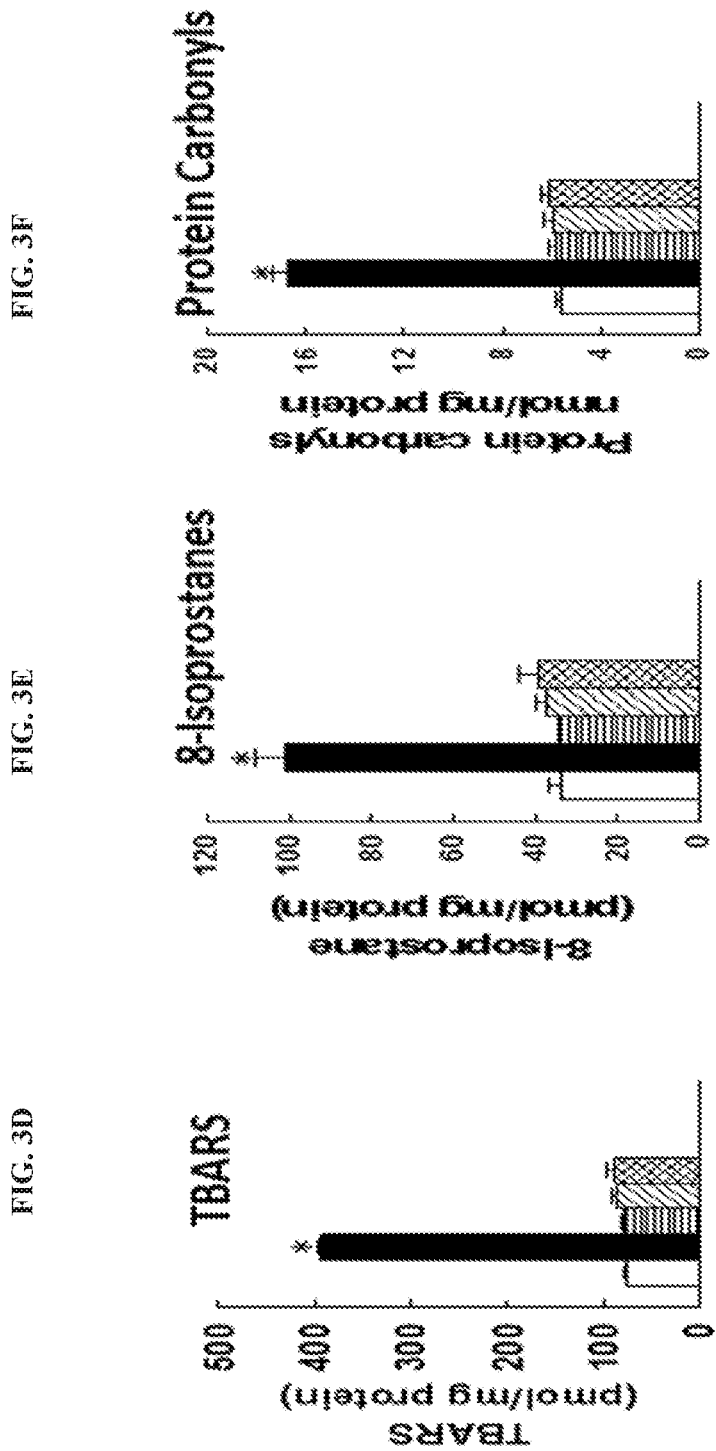
Figure 5A:
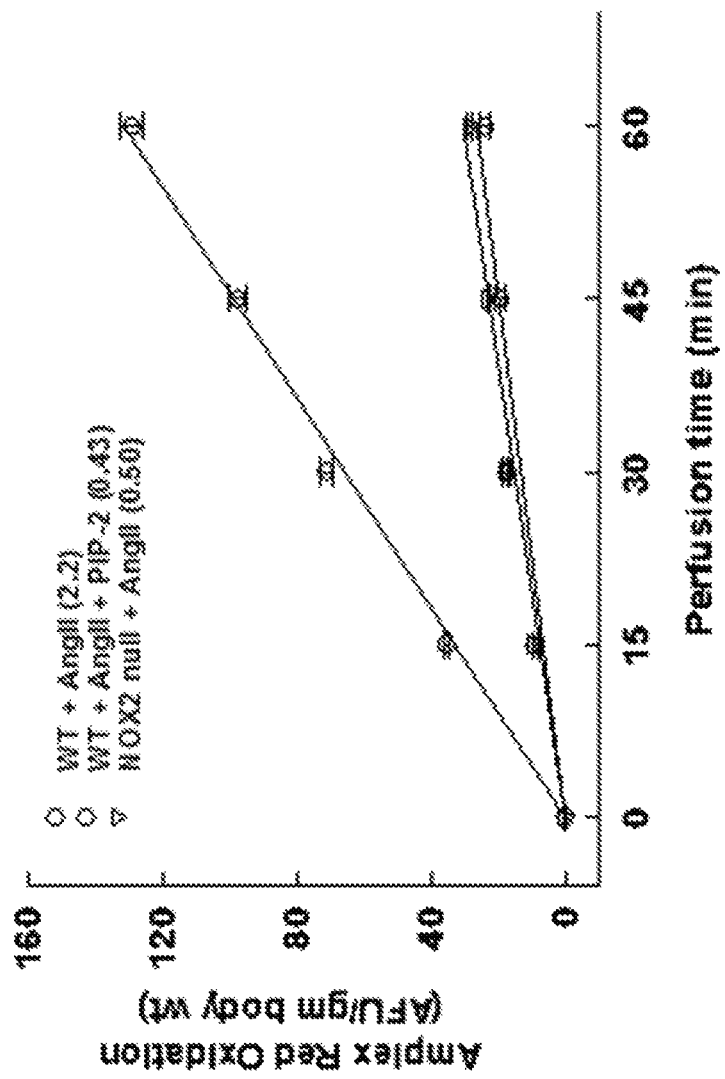
FIGS. 5A and 5B: PIP-2, incorporated within liposomes, was instilled intratracheally prior to lung isolation.
Figure 5B:
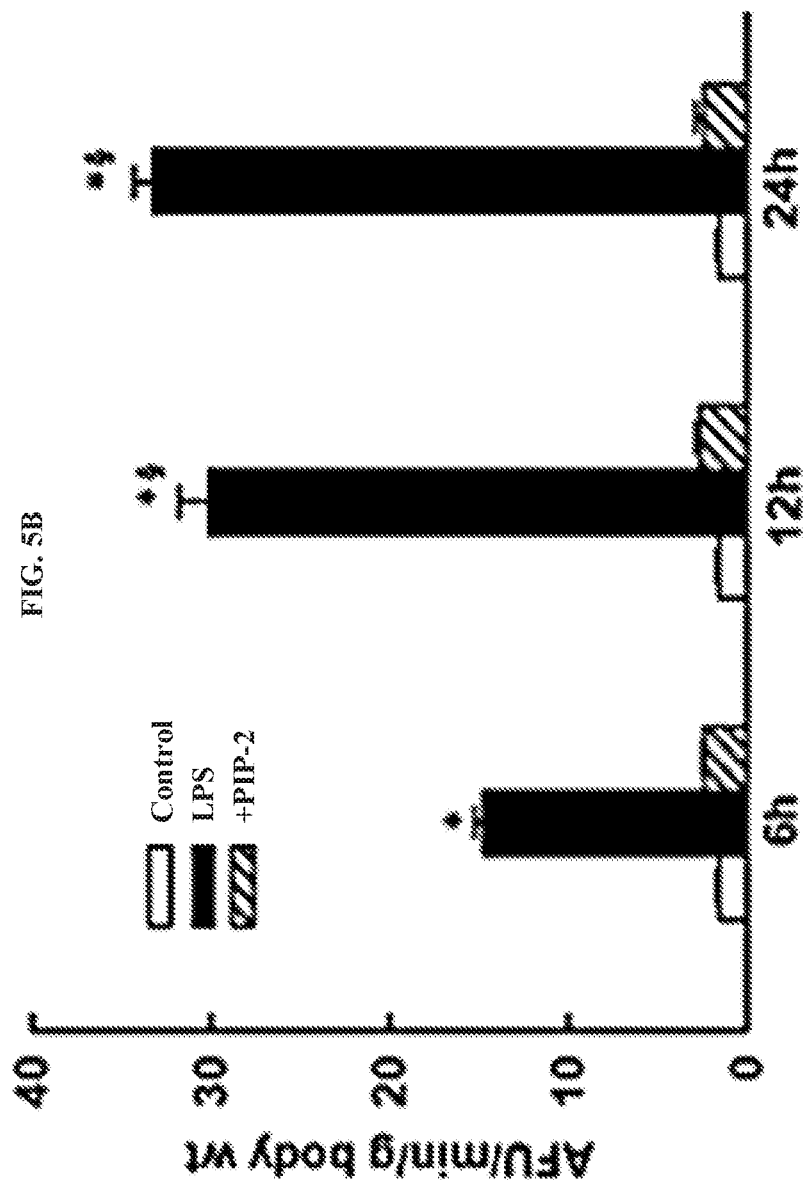
Figure 6:
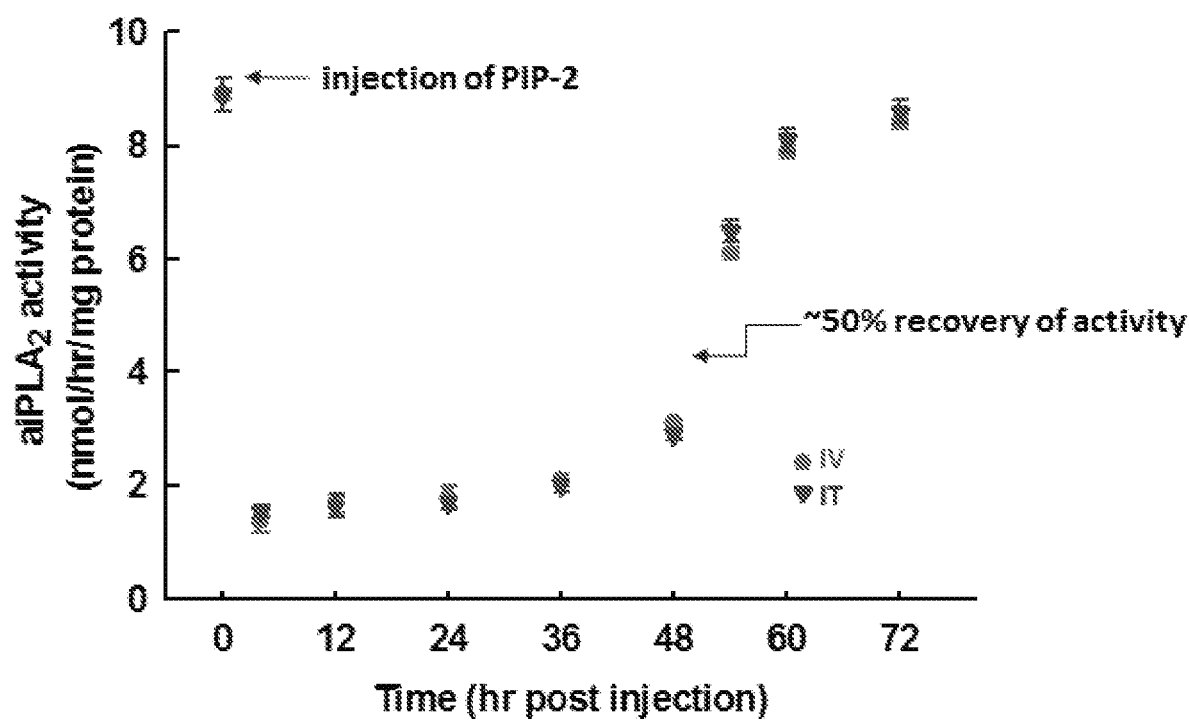
FIG. 6: PIP-2 in liposomes was administered to mice either intratracheally (IT) or intravenously (IV) at 0 time. Lungs were harvested at intervals between 4 and 72 h after the PIP-2 administration, homogenized, and analyzed for Prdx6-PLA2 activity. PIP-2 is effective by either the IT or IV route with a calculated ½ time for recovery of ~50 h. Results are mean+SE for N=3-4.

In various embodiments, the composition comprises a polypeptide consisting of SEQ ID NO: 1 LHDFRHQIL (PIP-2), SEQ ID NO: 2 LYEIKHQIL (PIP-4) or SEQ ID NO: 3 LYDIRHQIL (PIP-5). The composition of the invention may be provided to subjects as a pharmaceutical composition. Accordingly, in various embodiments, the composition further comprises a pharmaceutically acceptable carrier. As shown in FIG. 1, the polypeptides may be effectively administered in liposomes. Accordingly, in various embodiments, the polypeptide is encapsulated in one or more liposomes. In various embodiments, the composition is formulated for aerosol inhalation or intratracheal or intravenous injection. Appropriate pharmaceutically acceptable carriers as well as inhalable or injectable formulations are described elsewhere herein.

Methods of Treating Acute Lung Injury

In another aspect, the invention provides a method of treating acute lung injury in a subject, the method comprising administering to the subject an effective amount of a pharmaceutical composition comprising a polypeptide consisting of:

$$X^1X^2X^3X^4X^5LX^6X^7X^8X^9HQIL \quad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be T or E;
$X^6$ is H or Y;
$X^7$ is D or E;
$X^8$ is F or I; and
$X^9$ is R or K;

and a pharmaceutically acceptable carrier. In various embodiments, the polypeptide may be a polypeptide consisting of SEQ ID NO: 1 LHDFRHQIL, SEQ ID NO: 2 LYEIKHQIL or SEQ ID NO: 3 LYDIRHQIL. In various embodiments, the polypeptide administered to the subject is encapsulated in one or more liposomes. In various embodiments, the pharmaceutical composition is administered to the subject by aerosol inhalation or by intratracheal or intravenous injection.

Methods of Treating Sepsis

In another aspect, the invention provides a method of treating sepsis in a subject, the method comprising administering to the subject an effective amount of a pharmaceutical composition comprising a polypeptide consisting of:

$$X^1X^2X^3X^4X^5LX^6X^7X^8X^9HQIL \quad \text{SEQ ID NO: 4}$$

wherein:
$X^1$ may be present or absent and if present is E;
$X^2$ may be present or absent and if present is L;
$X^3$ may be present or absent and if present is Q;
$X^4$ may be present or absent and if present is A or T;
$X^5$ may be T or E;
$X^6$ is H or Y;

X⁷ is D or E;
X⁸ is F or I; and
X⁹ is R or K;
and a pharmaceutically acceptable carrier. In various embodiments, the polypeptide may be a polypeptide consisting of SEQ ID NO: 1 LHDFRHQIL, SEQ ID NO: 2 LYEIKHQIL or SEQ ID NO: 3 LYDIRHQIL. In various embodiments, the polypeptide administered to the subject is encapsulated in one or more liposomes. In various embodiments, the pharmaceutical composition is administered to the subject by aerosol inhalation or by intratracheal or intravenous injection. In various embodiments, the pharmaceutical composition is administered to the subject by intravenous injection.

Administration/Dosage/Formulations

The regimen of administration may affect what constitutes an effective amount. The therapeutic formulations may be administered to the subject either prior to or after the onset of injury. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a lung injury in the patient. An effective amount of the therapeutic compound necessary to achieve a therapeutic effect may vary according to factors such as the state of the disease or disorder in the patient; the age, sex, and weight of the patient; and the ability of the therapeutic compound to treat or prevent acute lung injury in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion or breakdown of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a lung injury in a patient.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of acute lung injury in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of acute lung injury in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such treatment regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Activity of PIP Peptides In Vivo

Mice were injected with PIP-2 (2 ug/g body wt) in liposomes (see FIG. 1) either IT (FIG. 1A) or IV (FIG. 1B); these liposomes contained tracer [$^3$H] in the 9,10 position of the sn-2 palmitate of DPPC. The lungs were removed from mice and studied in an isolated system. The slope of the lines indicates the production of oxidants ($H_2O_2$).

PIP-2 in liposomes injected IV or IT inhibits Prdx6 activity of the lung homogenate. Maximal inhibition was seen within 4 hours after administration of PIP-2. Recovery from inhibition began at ~36 hours and was complete by 48 hours. Results are similar for PIP-1,2,4 (PIP-3 and -5 were not tested). Based on the mouse results, PIP-2 or 4 could be administered once every 24-36 hours to maintain maximal inhibition of Prdx6 activity and NOX2 activation. Effectiveness requires liposomes for peptide delivery. Inhibition after IT or IV administration was similar. The data are presented in Tables 4-6, below.

TABLE 4 aiPLA2 activity of mouse lung at 24 hours after injection of PIP-4 IV with and without liposomes for delivery

|  | aiPLA$_2$ activity nmol/hr/mg prot |
| --- | --- |
| Control (liposomes only) n = 3 | 8.81 ± 0.2 (n = 3) |
| PIP-4 (in liposomes) | 1.55 ± 0.02 (n = 3) |
| PIP-4 (alone, no liposomes) | 8.43 ± 0.23 (n = 3) |

PIP-4 = 2 μg/g wt of mice.
Mean +/− SE; n = 3.

TABLE 5 aiPLA2 activity of mouse lung homogenate at increasing time after IT or IV injection of PIP-2: Persistence in vivo

| Time (H), post injection | Intratracheal (IT) aiPLA$_2$ activity, nmol/hr/mg protein | Intravenous (IV) |
| --- | --- | --- |
| 0 | 8.84 ± 0.35 (100) | 8.85 ± 0.3 (100) |
| 4 | 1.56 ± 0.03 (18) | 1.45 ± 0.07 (16) |
| 12 | 1.61 ± 0.04 (18) | 1.58 ± 0.04 (18) |
| 24 | 1.63 ± 0.14 (18) | 1.77 ± 0.11 (20) |
| 36 | 2.04 ± 0.04 (27) | 2.14 ± 0.03 (24) |
| 48 | 2.95 ± 0.10 (33) | 3.03 ± 0.05 (34) |
| 72 | 8.78 ± 0.18 (99) | 8.49 ± 0.10 (96) |

TABLE 6

Prdx6-PLA2 activity of mouse lung homogenate at increasing time after IT or IV injection of PIPs

| Time, post injection | Intratracheal (IT)* PIP-1 Prdx6-PLA$_2$ activity nmol/hr/mg protein | Intravenous (IV) PIP-1 | IT* PIP-2 | IV PIP-4 |
| --- | --- | --- | --- | --- |
| 0 | 9.0 ± 0.2 | 8.8 ± 0.3 | 8.1 ± 0.3 | 8.0 ± 0.7 |
| 4 hr | 1.6 ± 0.1 | 1.4 | — | — |
| 12 hr | 1.6 ± 0.1 | 1.5 | — | — |
| 24 hr | 1.7 ± 0.2 | 1.8 ± 0.1 | 1.2 ± 0.02 | 1.1 ± 0.02 |
| 48 hr | 2.9 ± 0.2 | — | 3.0 ± 0.2 | 2.8 ± 0.2 |
| 72 hr | — | — | 8.3 ± 0.9 | 7.8 ± 1.2 |
| 96 hr | — | — | — | 8.1 ± 0.2 |

*Lungs were lavaged prior to assay to avoid possible effects of non-internalized SP-A peptide.

Example 2: Time Course of Injury after IT LPS

Bacterial (*E. coli*) lipopolysaccharide (LPS) was administered to wild type C57Bl/6 mice by intratracheal (IT) injection at 5 ug/g body wt. Mice were sacrificed at 12, 16, 24 or 48 hours after LPS as indicated. Lungs were removed and lavaged with saline through the trachea to obtain the BALF; the lung was then homogenized. Parameters measured were nucleated cells and protein in the BALF, thiobarbituric acid reactive substances (TBARS), 8-isoprostanes, and protein carbonyls in the lung homogenate, and the ratio of lung wet to dry weight (W/D). Values are mean±for n=4.

As shown in FIG. 2, increased cells in BALF reflect inflammation, protein in BALF and increased Wet/Dry weight ratio reflect altered alveolar permeability, TBARS and 8-isoprostanes reflect cell membrane lipid peroxidation, and protein carbonyls reflect tissue protein oxidation. These effects are all characteristic of the ALI syndrome. There is significant lung injury after a single dose of LPS that is essentially unchanged between 12-24 hours after LPS. Partial recovery is seen at 48 hours. Lung injury with LPS is relatively stable at 12-24 hours; presumably this reflects a balance between on-going lung injury and recovery processes. The data are presented in Table 7, below.

TABLE 7

Time course of injury after IT LPS

| Condition | # of cells in BALf (×10$^4$/g body wt) | Total Protein in BALf (μg/g body wt) | TBARS pmol/mg prot. | 8 - Isoprostanes pmol/mg prot | Protein carbonyls nmol/mg prot | Wet/Dry weight ratio of lung |
| --- | --- | --- | --- | --- | --- | --- |
| Control | 0.97 ± 0.06 | 77 ± 2 | 75 ± 2.3 | 0.33 ± 0.03 | 5.6 ± 0.2 | 5.61 ± 0.02 |
| LPS, sacrifice @12 hrs | 7.94 ± 0.54 | 153 ± 4 | 374 ± 14 | 1.01 ± 0.11 | 15.9 ± 0.7 | 8.35 ± 0.15 |
| LPS, sacrifice @16 hrs | 8.43 ± 0.15 | 156 ± 3 | 379 ± 2.2 | 1.05 ± 0.04 | 16.7 ± 0.4 | 8.32 ± 0.15 |
| LPS, sacrifice @24 hr | 8.57 ± 0.53 | 162 ± 2 | 368 ± 12 | 1.04 ± 0.13 | 16.4 ± 1.4 | 7.84 ± 0.34 |
| LPS, sacrifice @48 hr | 5.20 ± 0.2 | 107 ± 1 | 214 ± 9.4 | 0.75 ± 0.02 | 8.52 ± 0.3 | 6.39 ± 0.4 |

LPS 5 μg/g

Example 3: PIP-2 Protects Against Lung Injury

The IT model of acute lung injury (ALI) as shown in Table 9 was used to test the effects of PIP-2. PIP-2 (2 ug/g body wt) in liposomes was administered IT along with LPS (0 hours) or intravenously (IV) at 12 or 16 hours after LPS. IV administration of PIP-2 was used to avoid a second 'assault' on the trachea. Mice were sacrificed at 24 hours and lungs were evaluated for injury as described in Table 9.

Protection (%) against lung injury was calculated as [1−(injury with PIP-2−control)/(LPS alone−control)]. Results are mean±SE for n=4. *$P<0.01$ vs control. †$P<0.01$ vs no PIP, 24 hours.

As shown in FIG. 3, administration of PIP-2 along with LPS completely prevented lung injury when evaluated at 24 hours after LPS administration. PIP-2 administered at 12 or 16 hours after LPS provided about 85-95% protection against lung injury evaluated at 24 hours after LPS. The effects of PIP-2 are very dramatic. PIP-2 or PIP-4 prevents lung injury when administered at 0 time and when administered at 12-16 hours, prevents further injury allowing the damaged lung to heal during the interval between 12-16 hours after LPS and sacrifice @ 24 hours (h). Thus, PIP-2 and PIP-4 can both prevent as well as treat lung injury. The data for various markers of lung injury are presented in Tables 8-11.

TABLE 8

Effect of PIP-2 on inflammation and edema after LPS

| Condition | # of cells ×10⁴/ g wt | mg protein/ g wt | Wet/Dry lung weight ratio |
|---|---|---|---|
| Control No LPS | 0.95 ± 0.16 | 75 ± 1.3 | 5.59 ± 0.03 |
| LPS (IT) sacrifice@24 hrs | 8.67 ± 0.53 | 164 ± 2 | 8.10 ± 0.22 |
| LPS IT, PIP-2 IT@0 hrs Sacrifice at 24 hrs | 0.92 ± 0.02 | 71± | 5.50 ± 0.04 |
| LPS IT, PIP-2 IV@12 hr Sacrifice at 24 hrs | 1.45 ± 0.03 | 84 ± 1.2 | 5.95 ± 0.02 |
| LPS IT, PIP-2 IV @ 16 h, Sacrifice at 24 hrs | 1.43 ± 0.2 | 82.0 ± 1.2 | 6.19 ± 0.06 | n = 4, PIP-2 concentration (2 µg/g wt of mice), LPS 5 µg/g

TABLE 9

Effect of PIP-2 on lung tissue oxidation after LPS

| Condition | TBARS pmol/mg prot. | 8-Iso-prostanes pmol/mg prot | Protein carbonyls nmol/mg prot |
|---|---|---|---|
| Control (no LPS) | 75 ± 1.3 | 34 ± 3 | 5.6 ± 0.2 |
| LPS in liposomes (IT) Sacrifice@24 hrs | 381 ± 4.5 | 101 ± 7 | 16.9 ± 0.4 |
| LPS IT, PIP-2 IT@ 0 hrs Sacrifice at 24 hrs | 70 ± 2.1 | 31 ± 2 | 5.4 ± 0.1 |
| LPS IT, PIP-2 IV @12 hr Sacrifice at 24 hrs | 85 ± 5.2 | 38 ± 1 | 6.4 ± 0.2 |
| LPS IT, PIP-2 IV@16 h Sacrifice at 24 hrs | 89 ± 9.3 | 40 ± 1 | 6.4 ± 0.3 | n = 4, PIP concentration (2 µg/g wt of mice), LPS 5 µg/g

TABLE 10

Effect of PIP-4 on inflammation and edema after LPS

| Condition | # of cells ×10⁴/ g wt | µg protein/ g wt | Wet/Dry lung weight ratio |
|---|---|---|---|
| Control (PIP in Liposomes) | 0.96 ± 0.03 | 78 ± 2 | 5.59 ± 0.02 |
| LPS in liposomes (IT) sacrifice@24 hrs | 8.5 ± 0.46 | 166 ± 3 | 7.40 ± 0.31 |
| LPS IT, PIP-4 IT@ 0 hrs Sacrifice at 24 hrs | 0.95 ± 0.02 | 77 ± 3 | 6.1 ± 0.01 |
| LPS IT, PIP-4 IV@12 hr Sacrifice at 24 hrs | 1.46 ± 0.25 | 85 ± 2 | 5.94 ± 0.05 |
| LPS IT, PIP-4 IV @ 16 h, Sacrifice at 24 hrs | 1.44 ± 0.12 | 83 ± 1 | 6.12 ± 0.09 | n = 4; PIP concentration, 2 µg/g wt of mice, LPS 5 µg/g

TABLE 11

Effect of PIP-4 on lung tissue oxidation after LPS

| Condition | TBARS pmol/mg prot. | 8-Iso-prostanes pmol/mg prot | Protein carbonyls nmol/mg prot |
|---|---|---|---|
| Control (PIP in Liposomes) IT | 76 ± 2 | 34 ± 1 | 5.8 ± 0.2 |
| LPS in liposomes (IT) Sacrifice@24 hrs | 374 ± 4 | 1.02 ± 3 | 16.9 ± 0.4 |
| LPS IT, PIP-4 IT@ 0 hrs Sacrifice at 24 hrs | 78 ± 4 | 32 ± 2 | 5.9 ± 0.3 |
| LPS IT, PIP-4 IV @12 hr Sacrifice at 24 hrs | 84 ± 2 | 0.38 ± 1 | 6.4 ± 0.1 |
| LPS IT, PIP-4IV@16 h Sacrifice at 24 hrs | 85 ± 2 | 0.39 ± 1 | 6.4 ± 0.1 | n = 4, PIP concentration (2 µg/g wt of mice), LPS 5 µg/g

Example 4: PIP-2 is Stable as a Dry Powder aiPLA$_2$ activity was measured at intervals to determine how long the peptide could maintain its efficacy as an inhibitor of aiPLA$_2$ activity. The peptide was stable for the 4 months of observation.

TABLE 12

Activity of PIP-2 during 4 months storage as a dry powder at room temp. indicates stability.

| sample | aiPLA$_2$ Activity nmol/min/mg prot. |
|---|---|
| No PIP-2 | 100 ± 4.0 |
| PIP-2, 0 days | 29.7 ± 2.9 |
| 30 d | 31.1 ± 1.3 |
| 45 d | 31.8 ± 1.0 |
| 60 d | 32.8 ± 0.9 |
| 90 d | 29.9 ± 1.1 |
| 120 d | 31.9 ± 2.4 |
| No PIP-2, 120 d | 103 ± 4.7 |

Example 5

The materials and methods used in the following examples are here described.

Animals

C57Bl/6J or NADPH oxidase (Nox2) null mice were obtained from the Jackson Laboratories (Bar Harbor, ME) and were maintained under HEPA-filtered air with 12 h light/dark cycles in the facilities of the University of Pennsylvania Laboratory Animal Resources (ULAR).

Reagents

The estimated purity of the peptides, evaluated by mass spectroscopy, was >89%. Lipopolysaccharide (LPS) derived from *Escherichia coli* 0111:B4 cell membranes and purified by gel-filtration chromatography was obtained from Sigma-Aldrich (St. Louis, Mo., USA, cat # L3012). The amplex red/horseradish peroxidase (HRP) assay kit (cat. #A22188) and the carboxy adducts of reduced difluorofluorescein diacetate (DFF-DA, cat. #13293) were purchased from Life Technologies, Grand Island, NY, USA (through Thermo-Fisher Scientific). Angiotensin II (Ang II) was obtained from Bachem, Torrance, CA, USA (cat. #4095850.0005). Authentic lipids were purchased from Sigma-Aldrich, St. Louis, MO, USA and liposomes were prepared by evaporation to dryness followed by reconstitution in saline as previously described to reflect the composition of lung surfactant; the liposome composition was, in mol fraction, 0.5 dipalmitoylphosphatidylcholine (DPPC), 0.25 egg phosphatidylcholine (PC), 0.10 phosphatidylglycerol (PG) and 0.15 cholesterol. PIP-2 when added was 0.15 µg PIP-2/µg lipid.

Administration of LPS and PIP-2

Anesthesized mice were administered LPS (either 5 or 15 µg/g body weight) in 20 µl saline that was instilled into the lung through an endotracheal catheter placed at the level of the tracheal carina. We have shown previously that PIP-2 is ineffective if injected alone, while it inhibits aiPLA2 activity with a ½ time of ~50 h if encapsulated in liposomes. PIP-2 in liposomes was suspended in 20 µl saline for IV or IT injection. For studies to evaluate the effect of PIP-2 at zero time, LPS administration was followed by liposomes±PIP-2 also given by IT instillation. For studies to evaluate the effect of PIP-2 administered at later times after LPS, the liposomes±PIP-2 were given by injection into a retinal artery. This shift in route of administration was used to minimize damage to the mouse trachea that could occur with repeated tracheostomy and lead to untoward effects on the lung. The dose of PIP-2 used for treatment after intratracheal LPS was 2 µg/g mouse body weight; in control mice, this dose of PIP-2 has been shown to inhibit lung aiPLA$_2$ activity maximally for at least 24 h. We gave the second dose of PIP-2 at 12 h to be certain of maximal coverage and then went to every 24 h for PIP-2 administration. For the model of sepsis, LPS (15 µg/g body wt.) in 20 µl saline was injected intraperitoneally and mice were treated with IV PIP-2 at either 2 or 20 µg/g body wt; note that the initial dose of PIP-2 for this sepsis model was IV, not IT. We used the same times of PIP-2 administration in the sepsis model as were used for the IT LPS model. After recovery from anesthesia, all mice were maintained in the vivarium with access ad lib to food and water.

Evaluation of Lung Injury

At the end of each experiment with IT LPS (at either 24 or 120 h), surviving mice were sacrificed by exsanguination under anesthesia. Lungs in situ were cleared of blood by perfusion through the pulmonary artery and then were lavaged through the trachea with saline. The lung was then removed from the thorax for tissue assays. We evaluated the effect of LPS on lung injury by measuring the number of nucleated cells and the protein content in the lung bronchoalveolar lavage fluid (BALf), the lung wet to dry lung weight ratio using the left upper lobe of lung, and thiobarbituric-acid reactive products (TBARS), 8-isoprostanes, and protein carbonyls in the lung homogenate to determine the oxidation of lung tissue lipid and protein components. For studies of mouse mortality, survival plots were constructed using the Kaplan-Meier estimator.

Measurement of Lung ROS Production and aiPLA$_2$ Activity

The effect of the PIPs on ROS production in control (untreated) lungs was determined in vitro with isolated perfused lungs. PIP-2 in liposomes was administered at 2 µg/g mouse weight by the IV route. After 30 mins, mice were anesthesized and lungs were isolated, cleared of blood, and perfused in a recirculating system with perfusate containing Ang II (50 µM) as a Nox2 activator and Amplex red plus horseradish peroxidase to detect ROS. Lungs from wild type mice and lungs from NOX2 null mice that were not treated with PIP-2 were used as controls. The basal rate of ROS production was evaluated with WT lungs that were perfused in the absence of AngII. The perfusion protocol included a 15 min equilibration period followed by a 60 min experimental period. Aliquots of perfusate were taken at 15 min intervals and analyzed by fluorescence for resorufin ($\lambda_{excitation}$ 568 nm, $\lambda_{emission}$ 581 nm), the product of Amplex red oxidation. The rate of Amplex red oxidation was calculated and expressed as arbitrary fluorescence units (AFU) with normalization to mouse body wt. There was a low rate of Amplex red oxidation in the absence of HRP in the perfusate (~7% of the AngII-stimulated fluorescence), indicating a non-ROS-mediated oxidation of the fluorophore; this value was subtracted to obtain the reported values.

To determine lung ROS production after LPS treatment, intact mice were treated with LPS (5 µg/g)±PIP-2 (2 µg/g). Mice were anesthesized at 6, 12, or 24 h after treatment with LPS and lungs in situ were cleared of blood and then perfused for 10 mins with saline solution containing the fluorophore DFF-DA that is hydrolyzed intracellularly to DFF. Lungs were then homogenized, and fluorescence of the homogenate was measured at Ex 495 nm, Em 525 nm. Lung fluorescence was expressed as AFU per minute of perfusion with normalization to the mouse body wt.

Statistical Analysis

Data are expressed as means±standard error (SE). The slope of linear plots was calculated by the least mean squares method. SigmaStat software (Jandel Scientific, San Jose, CA) was used assess statistical significance. Mean values for group differences were evaluated by 1-way ANOVA followed by the Bonferroni post hoc test. For comparison of 2 groups, means were compared by the Student t-test. Differences between mean values were considered statistically significant at $P<0.05$.

Results:

Inhibition of lung ROS production by PIP.

Figure 8:
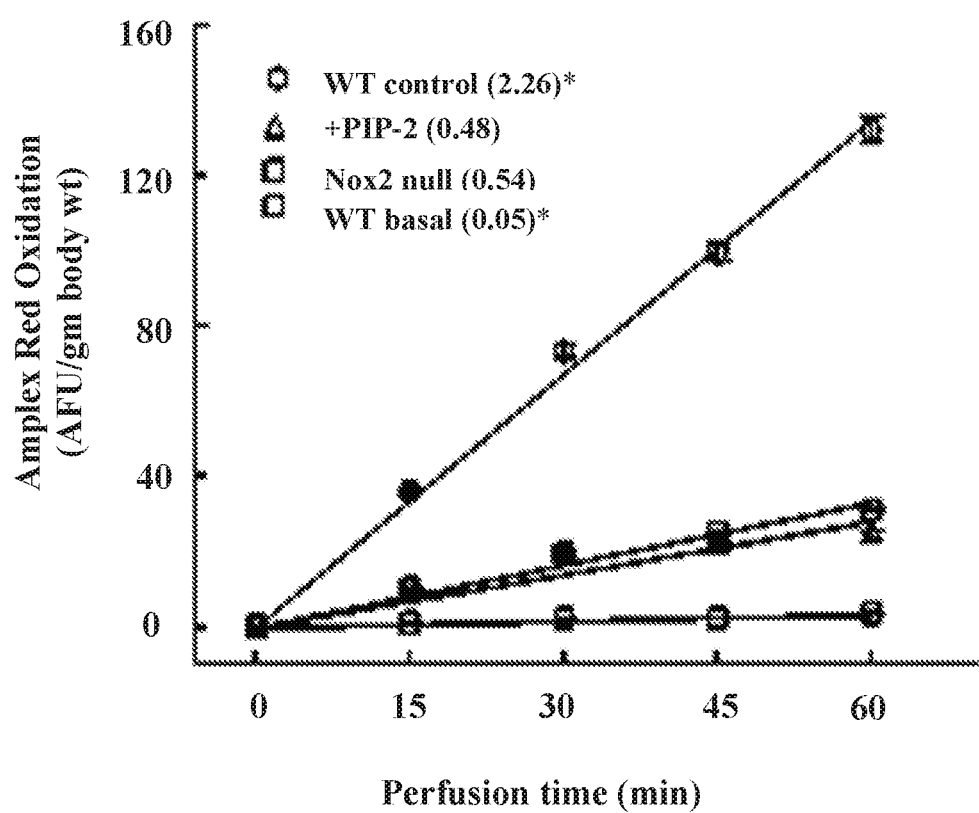
FIG. 8: PLA2 inhibitory peptide (PIP-2) inhibits ROS production stimulated by angiotensin II (Ang II) in isolated perfused mouse lung. PIP-2 (2 µg/g body weight) was administered to intact wild type (WT) mice by the IV route. WT basal, WT control and NOX2 null did not receive peptide. After 30 mins, lungs were isolated from anesthesized mice and perfused in a recirculating system with added Ang II (50) as a Nox2 activator and Amplex red plus horseradish peroxidase to detect perfusate ROS. WT basal lungs were not stimulated with Ang II. After a 15 min equilibration period (called zero time), aliquots were taken at 15 min intervals for analysis of fluorescence. Each plotted point represents the mean±SE for n=3. The lines were drawn by the least mean squares method. The mean rates of ROS reduction calculated from the slope of each line are indicated in parentheses. *P<0.05 vs the other 3 slopes.

In order to confirm the inhibitory effect of PIP compounds on NOX2 activation, we studied ROS production by the isolated perfused lung in the presence of Ang II, a known activator of NOX2. Amplex red oxidation was used as an index of ROS production. There was a very low baseline rate of ROS production in perfused lungs under control conditions, i.e, no added stimulant of NOX2 activity (FIG. 8, WT basal). ROS production was markedly increased with the addition of Ang II to the perfusate to activate NOX2 (FIG. 8, WT control). ROS generation was decreased by 76% in NOX2 null compared to WT lungs, indicating that NOX2 is the major source of ROS entering the perfusate after Ang II stimulation. The addition of PIP-2 (in liposomes) to WT lungs inhibited ROS production (~75%) similarly to NOX2 null, as shown previously. Thus, PIP-2 resulted in essentially total inhibition of NOX2-mediated ROS generation.

Figure 9A:
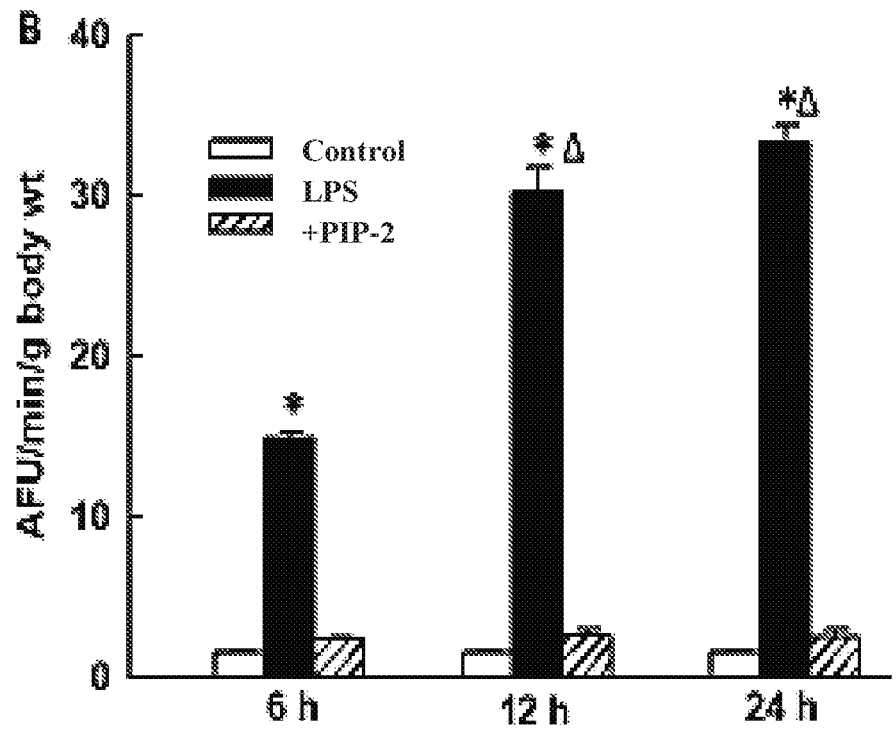
Figure 9B:
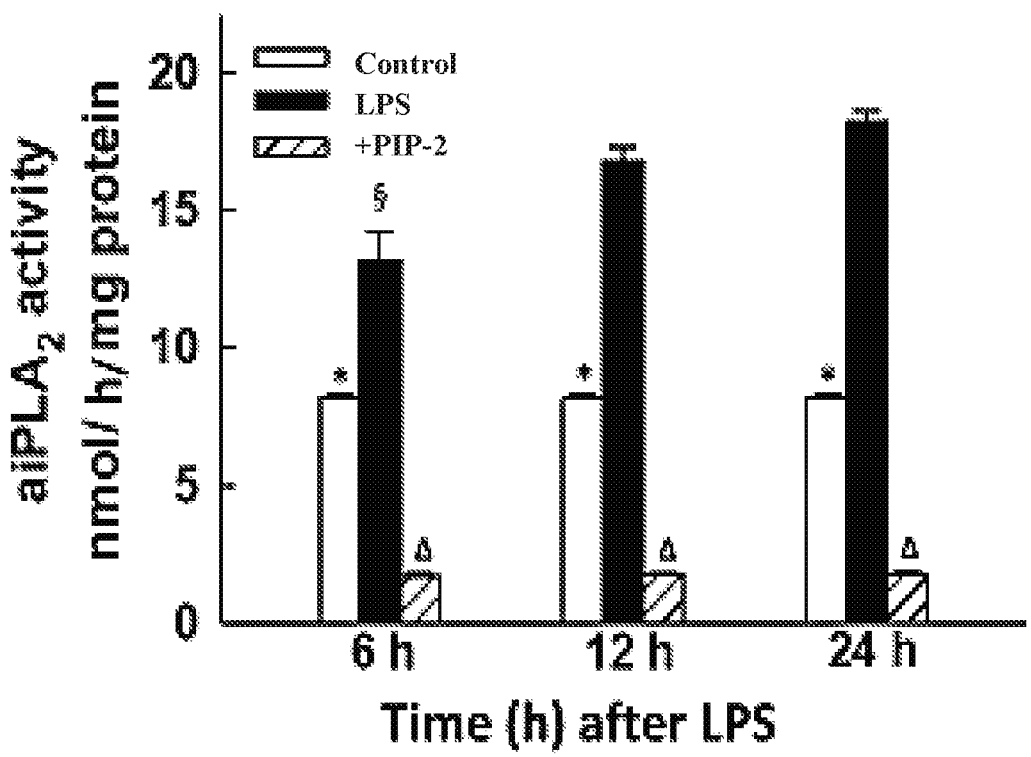

We next determined the effect of PIP-2 (in liposomes) on aiPLA$_2$ activity and ROS production in lungs following LPS. These parameters were determined at 6, 12, and 24 h after the administration of IT LPS. aiPLA2 activity in the lung homogenate increased by ~50% compared to control at 6 h after treatment with LPS and increased by another 50% at 12 and 24 h FIG. 9A). We used an intracellular fluorophore (DFF-DA) to determine lung ROS generation. ROS-induced fluorescence was very low in the non-LPS-treated control lung but was increased ~10-fold at 6 h and ~20-fold at both 12 and 24 h in the LPS-treated mouse lungs (FIG. 9B). This increase in lung DFF fluorescence after LPS could be slightly underestimated due to signal dilution from the presence of edema in these lungs (see below). Pre-treatment of mice with PIP-2 before LPS administration resulted in a dramatic decrease in aiPLA2 activity and in ROS-generated fluorescence at all 3 time periods to values similar to the non-LPS-treated control. These results indicate that intratracheal administration of LPS results in increased ROS production in the lung that is maintained for at least 24 h and can be inhibited almost totally by pre-treatment of lungs with PIP-2.

Time Course for LPS-Mediated Lung Injury

The sensitivity to LPS-mediated injury varies significantly among mouse strains. For this study, we determined the course of lung injury for C57Bl/6J mice given IT LPS at 5 μg/g body weight (FIGS. 2A-2F). Lungs showed considerable injury when evaluated at 12 h after LPS as indicated by increased nucleated cells in the BALf, increased BALf protein, and increased wet to dry lung weight ratio ($p<0.05$). These results are compatible with lung inflammation (cells in BALf), alteration of the alveolar-capillary permeability barrier (BALf protein), and lung fluid accumulation (lung wet/dry weight). The increase in lung tissue TBARS, 8-isoprostanes, and protein carbonyls indicates oxidative stress with oxidation of lung tissue lipid and protein components. These indices of lung injury showed similar values at 12, 16 or 24 h after LPS (FIGS. 2A-2F) indicating that the degree of lung injury was essentially stable at 12-24 h after this non-lethal dose of LPS. Partial recovery (~50%, $p<0.05$) in the indices of lung injury was seen at 48 h although they were still elevated compared with control ($p<0.05$).

Effect of PIP-2 on LPS-Mediated Lung Injury

To study the effect of PIP-2 administration on lung injury, mice were treated with LPS (5 μg/g body weight) given IT. The dose of LPS was chosen based on our previous studies using the same batch of LPS that showed a relatively low level of lung injury with 1 μg/g body wt and greater injury with no significant mortality using 5 μg LPS/g body wt. PIP-2 (2 μg/g body weight in liposomes) was administered at 0, 12, or 16 h after LPS. We have shown previously that this dose of PIP-2 can inhibit lung aiPLA2 activity by ~90% for at least 24 h. PIP-2 was given IT at time zero and IV at 12 or 16 h in order to avoid excessive damage to the trachea. Animals were sacrificed and lungs were examined at 24 h after LPS. All indices of lung injury, reflecting lung inflammation, alveolar-capillary barrier dysfunction, lung fluid accumulation, and tissue oxidative stress, were elevated in LPS-treated mice as compared to control ($p<0.05$). PIP-2 administered at 0 time completely prevented lung injury when assessed at 24 h after LPS (FIGS. 3A-3F). Indices of tissue injury in lungs of mice treated with PIP-2 at 12 and 16 h also were markedly decreased compared to LPS alone and values were not significantly different from control values (FIGS. 3A-3F). Since lung injury was present in lungs at 12 and 16 h after LPS, the normal values at 24 h in lungs from LPS treated mice given PIP-2 at 12 or 16 h can only mean that lungs were able to recover fully from their injury during the 8 to 12 h interval between the administration of PIP-2 and examination of the lungs.

PIP-2 treatment prevents mouse mortality with high dose LPS.

Although mice treated with low dose LPS (5 μg/g body wt) suffer significant lung injury, it is transient and essentially all mice will recover from the insult (not shown). In order to test the effect of PIP-2 treatment with a more severe injury model, mice were administered a higher dose of LPS (15 μg/g body weight). The survival data is plotted with the initial PIP-2 treatment as 0 time; LPS was administered 12 h before PIP-2 (−12 h that is off of the graph in FIG. 7A and FIG. 7B). At this higher dose of LPS, mice that were treated with placebo (liposomes alone) showed 73% mortality during the 24 hr after LPS and 100% mortality by 48 h. For the treatment arm, PIP-2 was administered to mice at 12, 24, 48, 72 and 96 h after LPS and mice were sacrificed at 120 h; PIP-2 treated mice showed only 17% mortality (83% survival) at 36 h after the start of PIP-2 treatment and had no further mortality during the period of observation. In addition to the effect on mortality, a marked difference was observed in the behavior of mice that had received PIP-2 after LPS with a return of most mice to normal physical activity by 12 h after receiving PIP-2. Indices of lung injury in treated mice that were sacrificed at 120 h after LPS showed no abnormality (Table 13).

TABLE 13

Lung injury is repaired in mice that survive high dose LPS.

|  | BALf cells ×10⁴/g body wt. | BALf protein μg/g wt | Wet/Dry ratio | TBARS pmol/mg prot | 8-isoprostanes pmol/mg prot | Protein carbonyls nmol/mg prot |
|---|---|---|---|---|---|---|
| Control (no LPS) | 0.95 ± 0.04 | 75 ± 1.3 | 5.59 ± 0.03 | 76 ± 6 | 34 ± 3 | 5.6 ± 0.2 |
| LPS + PIP-2 | 0.96 ± 0.40 | 78 ± 2.2 | 5.34 ± 0.03 | 77 ± 1 | 34 ± 3 | 5.6 ± 0.2 |

Mice were instilled IT with LPS (15 μg/g wt); PIP-2 (2 μg/g body wt) in liposomes was injected (IV) at the times shown in FIG. 7A. Five of the surviving mice were sacrificed at 120 h after LPS; control mice were given liposomes but not LPS. BALf, bronchoalveolar lavage fluid; TBARS, thiobarbituric reactive substances. Values are mean±SE for N=4 for control and N=5 for LPS+PIP-2. None of the mean values for LPS+PIP-2 are statistically different ($p>0.05$) than the corresponding control.

We next evaluated the effect of PIP-2 in mice given LPS (15 μg LPS/g body wt.) by the intraperitoneal route as a model for ALI associated with systemic sepsis. We chose the dose of LPS based on our previous study that showed 60% mortality with 10 ug LPS/g body wt; our goal was to produce 100% mortality in the placebo-treated mice, similar to that seen with the high dose IT LPS study. Survival of placebo-treated mice (liposomes only) was less than 40% at 24 h after LPS and 100% of mice were dead by 48 h (FIG. 7B). By contrast, treatment of mice with PIP-2 (2 μg/g body wt) increased survival at 36 h after LPS to 86% and 43% of mice fully recovered. With a higher dose of PIP-2 (20 µg/g body wt.), the long term survival rate was significantly greater at 70%. Thus, PIP-2 markedly increased mouse survival in this model of ALI associated with systemic sepsis.

ALI is a serious disease syndrome with a mortality rate of ~40%. Inflammation is an important factor that can amplify the lung injury associated with the primary insult. To date, there is no approved pharmacologic treatment for the inflammatory component of the syndrome. The mechanisms for lung injury during lung inflammation are complex, but excessive ROS production appears to play a major role. We have shown previously that the aiPLA2 activity of Prdx6 is required for activation of ROS production by NOX2 and have described several nonapeptides derived from lung surfactant protein A (SP-A) sequences that inhibit aiPLA$_2$ activity and thereby inhibit the activation of NOX2 in lung cells. The present study confirms that these peptides, called PLA$_2$-inhibitory peptides (PIP-2, PIP-4, and PIP-5) inhibit ROS production by AngII-activated NOX2 in the isolated mouse lung. Although PIP-2 appeared to be slightly more active that the other 2, all 3 PIP compounds were effective as inhibitors, presumably reflecting in part the high degree of conservation of the Prdx6 amino acid sequence among species. We have demonstrated that the site for binding of the 16 amino acid precursor of the PIPs is to the amino acid sequence comprising amino acids 195 to 204 of Prdx6. The sequence for this segment of human Prdx6 is: SEQ ID NO: 34 195-EEEAKKLFPK-204; the corresponding mouse sequence is the same for 8 of the 10 amino acids with Q rather than K at position 200 and C rather than L at position 201. We chose PIP-2, the PIP that was derived from the relevant sequence in human SP-A, for subsequent investigations. The PIP-2 amino acid sequence is: SEQ ID NO:1 LHDFRHQIL.

The primary goal of the present study was to evaluate the effect of PIP-2 on lung injury associated with the intratracheal administration of LPS. We first demonstrated that PIP-2 markedly inhibited AngII-mediated ROS generation; AngII is a known activator of NOX2 and, as we have shown previously, activation requires aiPLA$_2$ activity. We then showed that treatment with LPS resulted in both a marked increase in aiPLA2 activity of the lungs and also a marked increase in ROS production through the activation of NOX2; both the LPS-mediated increase in aiPLA2 activity and ROS production also were inhibited by PIP-2.

The first study of PIP-2 effectiveness in the lung injury model was the concurrent administration of PIP-2 with LPS which markedly protected against subsequent lung injury. Measurements to evaluate acute lung injury following LPS included: a) nucleated cells in BALf (inflammation); b) protein in BALf (alveolar-capillary permeability); c) lung wet to dry weight ratio (lung edema); and d) lung TBARS, 8-isoprostanes, and protein carbonyls (oxidation of tissue lipids and proteins). All of these indices of injury were significantly elevated in lungs that were evaluated at 12-24 h after administration of LPS. However, none of these indices of tissue injury was altered in lungs when PIP-2 was administered concurrently with LPS. Thus, PIP-2 can prevent ALI associated with LPS administration in mice.

The next study investigated the effect of PIP-2 administered at 12 or 16 h after administration of LPS as a treatment (as opposed to preventative) modality. As shown in FIGS. 3A-3F, the tissue injury associated with non-lethal LPS is maximal at this time. With PIP-2 administration at either 12 or 16 h after LPS, parameters of lung injury had returned to essentially normal values when examined at 24 h after LPS. Our conclusion from this study is that PIP-2 prevented on-going lung injury associated with LPS and allowed the lung to repair itself during the 8-12 h between PIP-2 administration and sacrifice of the animal.

Our final study was to evaluate the effects of PIP-2 on mouse lung function and survival following the administration of a lethal dose of LPS. PIP-2 administered every 12-24 h following administration of LPS led to a dramatic improvement of mouse behavior, markedly reduced mouse mortality, and resulted in return of the indices of lung injury to normal values. Thus, the nonapeptide inhibitor of the PLA$_2$ activity of Prdx6 prevented ROS generation subsequent to NOX2 activation and prevented mortality associated with the administration of a lethal dose of LPS. These results indicate that PIP-2 can both prevent and treat the mouse model of LPS-induced ALI.

The present results with PIP-2 give a similar conclusion as our previous studies that showed protection in LPS-induced ALI using several different means to inhibit aiPLA$_2$ activity and subsequent activation of NOX2. These have included: a) administration of MJ33, a lipid inhibitor of aiPLA$_2$ activity; b) use of Prdx6 null mice (a less than perfect model since the peroxidase activity of Prdx6 is also lost); and c) mice with mutation of amino acid D140 in Prdx6, an essential component of the aiPLA$_2$ active site. The MJ33 inhibited mouse, the D140A mutant mouse, and the PIP-2 treated mouse all retain the peroxidase activity of Prdx6 while this activity is abolished in the Prdx6 null mouse. In these previous studies, LPS was administered by the IT route in a) and b) as a model for direct lung injury and by the intraperitoneal route in c) as a model for non-infectious sepsis. We have proposed that the mechanism for the protection afforded by PIP-2 is its inhibition of the aiPLA$_2$ activity of Prdx6 by allosteric effects resulting from binding of the peptide to Prdx6. The PIP peptides do not inhibit other lung PLA$_2$ enzymes as demonstrated experimentally and as expected based on dissimilarity of potential binding sites on the different proteins. The inhibition of aiPLA$_2$ activity prevents the generation of lysoPC and its downstream products, thereby preventing the activation of Rac, a necessary co-factor for Nox2 activation. Interestingly, the cholesterol-lowering drug simvastatin also inhibits the activation of Rac, and has been shown to inhibit ROS production by endothelial cells and to be protective in mouse models of LPS-induced ALI. Although there is no definitive evidence as yet, it is possible that inhibition of Rac activation has salutary effects on non-ROS mediated manifestations of ALI in addition to its effect on NOX2 activation.

The present and previous studies have shown that NOX2 is a major source of ROS in lungs and that the enzyme is activated in the presence of LPS. In addition to the LPS model, ROS generation by NOX2 has been shown to play a central role in several other related as well as disparate animal models of ALI including gram negative sepsis, endotoxin, severe trauma, hemorrhagic shock, and oleic acid instillation. Presumably, a major manifestation of the oxidant stress associated with NOX2 activation is the oxidation of tissue macromolecules as shown in the present study. However, another important pathophysiological role associated with NOX2-derived ROS is based on evidence that ROS are responsible for the signals leading to neutrophil recruitment to the lung and the resultant lung inflammation that is characteristic of ALI. The marked decrease in nucleated cells in BALf after treatment with PIP-2 suggests that this function of ROS is important for the recovery from lung injury. In that respect, a peptide inhibitor of the myristoylated alanine-rich C kinase substrate (Marcks) protein also protects against lung injury with LPS in mice. Although this latter peptide has not been shown to inhibit NOX2 activation, its effects may be mediated through altered cellular motility that prevents PMN influx into the lung. Thus, PIP-2, simvastatin, the Marcks protein inhibitor, and possibly inhibitors of NOX2 such as apocynin all may prevent PMN influx into the lung after LPS, thereby reversing inflammation and the associated lung injury.

Based on the present results, the peptide inhibitors of NOX2 activation could be effective as preventative agents for patients at risk for ALI as well as for treatment of patients with established ALI. Although toxicity of these small peptides is not expected based on their normal expression in lungs as a component of the SP-A protein, that still must be investigated. The antigenic potential of the peptide theoretically is low, but that will need to be confirmed in humans. Other possible side effects of the peptides include those associated with inhibition of Rac activation as well as loss of the signaling and regulatory functions of ROS. Of note, no major effects have been reported as yet that could be related to the inhibition of Rac with the widely used drug, simvistatin. A potentially more important "side-effect" of treatment with PIP could be the effect of inhibited ROS production on the bactericidal activity of inflammatory cells (PMN and AM) that use superoxide anion generated through activity of NOX2 for the killing of bacteria. Further, it has been shown that some antibiotics require ROS for maximal efficacy. Despite the theoretical possibility of an altered response to infection, an inhibitor of NOX2 activation did not decrease bactericidal activity of PMN in an LPS model of ALI. This may reflect the ability of non-NOX2 pathways to compensate for the loss of NOX2-derived ROS. Although this would emphasize the important role for antibiotic coverage in patients being treated with NOX2 inhibitors, it is important to note that the use of antibiotics alone has not been effective in reducing mortality with this disease to a value significantly below 40%.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a polypeptide consisting of:

$X^1X^2X^3X^4X^5LX^6X^7X^8X^9HQIL$  SEQ ID NO: 4 wherein:
- $X^1$ may be present or absent and if present is E;
- $X^2$ may be present or absent and if present is L;
- $X^3$ may be present or absent and if present is Q;
- $X^4$ may be present or absent and if present is A or T;
- $X^5$ may be present or absent and if present is T or E;
- $X^6$ is H or Y;
- $X^7$ is D or E;
- $X^8$ is F or I; and
- $X^9$ is R or K.

2. The composition of claim 1, wherein the polypeptide is selected from the group consisting of:

ELQTELYEIKHQIL,  SEQ ID NO: 5

QTELYEIKHQIL  SEQ ID NO: 6
and

ELYEIKHQIL.  SEQ ID NO: 7

3. The composition of claim 1, wherein the polypeptide is selected from the group consisting of:

LHDFRHQIL,  SEQ ID NO: 1

LYEIKHQIL  SEQ ID NO: 2
or

LYDIRHQIL.  SEQ ID NO: 3

4. The composition of claim 1, further comprising a pharmaceutically acceptable carrier.

5. The composition of claim 1, wherein the polypeptide is encapsulated in one or more liposomes.

6. The composition of claim 1, wherein the composition is formulated for aerosol inhalation or intratracheal or intravenous injection.

7. A method of treating acute lung injury in a subject, the method comprising administering to the subject an effective amount of a pharmaceutical composition comprising a polypeptide consisting of:

$X^1X^2X^3X^4X^5LX^6X^7X^8X^9HQIL$  SEQ ID NO: 4 wherein:
- $X^1$ may be present or absent and if present is E;
- $X^2$ may be present or absent and if present is L;
- $X^3$ may be present or absent and if present is Q;
- $X^4$ may be present or absent and if present is A or T;
- $X^5$ may be T or E;
- $X^6$ is H or Y;
- $X^7$ is D or E;
- $X^8$ is F or I; and
- $X^9$ is R or K;

and a pharmaceutically acceptable carrier.

8. The method of claim 7, wherein the polypeptide is selected from the group consisting of:

ELQTELYEIKHQIL,  SEQ ID NO: 5

QTELYEIKHQIL  SEQ ID NO: 6
and

ELYEIKHQIL.  SEQ ID NO: 7

9. The method of claim 7, wherein the polypeptide is selected from the group consisting of:

LHDFRHQIL,  SEQ ID NO: 1

LYEIKHQIL  SEQ ID NO: 2
or

LYDIRHQIL.  SEQ ID NO: 3

10. The method of claim 7, wherein the polypeptide is encapsulated in one or more liposomes.

11. The method of claim 7, wherein the pharmaceutical composition is administered to the subject by aerosol inhalation or by intratracheal or intravenous injection.

12. A method of treating sepsis in a subject, the method comprising administering to the subject an effective amount of a pharmaceutical composition comprising a polypeptide consisting of:

$X^1X^2X^3X^4X^5LX^6X^7X^8X^9HQIL$  SEQ ID NO: 4 wherein:
- $X^1$ may be present or absent and if present is E;
- $X^2$ may be present or absent and if present is L;
- $X^3$ may be present or absent and if present is Q;
- $X^4$ may be present or absent and if present is A or T;
- $X^5$ may be T or E;
- $X^6$ is H or Y;
- $X^7$ is D or E;
- $X^8$ is F or I; and
- $X^9$ is R or K;

and a pharmaceutically acceptable carrier.

13. The method of claim 12, wherein the polypeptide is selected from the group consisting of:

```
                                    SEQ ID NO: 5
ELQTELYEIKHQIL,

SEQ ID NO: 6
QTELYEIKHQIL
and

SEQ ID NO: 7
ELYEIKHQIL.
```

14. The method of claim 12, wherein the polypeptide is selected from the group consisting of:

```
                                    SEQ ID NO: 1
LHDFRHQIL,

SEQ ID NO: 2
LYEIKHQIL
or

SEQ ID NO: 3
LYDIRHQIL.
```

15. The method of claim 12, wherein the polypeptide is encapsulated in one or more liposomes.

16. The method of claim 12, wherein the pharmaceutical composition is administered to the subject by aerosol inhalation or by intratracheal or intravenous injection.

17. The composition of claim 1, wherein the polypeptide consists of the amino acid sequence of SEQ ID NO: 1.

18. The method of claim 7, wherein the polypeptide consists of the amino acid sequence of SEQ ID NO: 1.

19. The method of claim 12, wherein the polypeptide consists of the amino acid sequence of SEQ ID NO: 1.

\* \* \* \* \*

SEQUENCE LISTING

```
<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 1

Leu His Asp Phe Arg His Gln Ile Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 2

Leu Tyr Glu Ile Lys His Gln Ile Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 3

Leu Tyr Asp Ile Arg His Gln Ile Leu
1               5

<210> SEQ ID NO 4
<211> LENGTH: 14
<212> TYPE: PRT
<213> ORGANISM: Artificial Sequence
<220> FEATURE:
<223> OTHER INFORMATION: Inhibitory peptide.
```

```
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid

<400> SEQUENCE: 4

Xaa Xaa Xaa Xaa Xaa Leu Xaa Xaa Xaa Xaa His Gln Ile Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Inhibitory peptide.

<400> SEQUENCE: 5

Glu Leu Gln Thr Glu Leu Tyr Glu Ile Lys His Gln Ile Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Inhibitory peptide.

<400> SEQUENCE: 6

Gln Thr Glu Leu Tyr Glu Ile Lys His Gln Ile Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Inhibitory peptide.

<400> SEQUENCE: 7

Glu Leu Tyr Glu Ile Lys His Gln Ile Leu
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Inhibitory peptide.

<400> SEQUENCE: 8

Asp Glu Glu Leu Gln Ala Thr Leu His Asp Phe Arg His Gln Ile Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Inhibitory peptide.

<400> SEQUENCE: 9

Asp Glu Glu Leu Gln Thr Glu Leu Tyr Glu Ile Lys His Gln Ile Leu
1               5                   10                  15
```

```
<210> SEQ ID NO 10
<211> LENGTH: 14
<212> TYPE: PRT
<213> ORGANISM: Artificial Sequence
<220> FEATURE:
<223> OTHER INFORMATION: Inhibitory peptide.

<400> SEQUENCE: 10

Glu Leu Gln Thr Glu Leu Tyr Glu Ile Lys His Gln Ile Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Inhibitory peptide.

<400> SEQUENCE: 11

Gln Thr Glu Leu Tyr Glu Ile Lys His Gln Ile Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Inhibitory peptide.

<400> SEQUENCE: 12

Glu Leu Tyr Glu Ile Lys His Gln Ile Leu
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Inhibitory peptide.

<400> SEQUENCE: 13

Tyr Glu Ile Lys His Gln Ile Leu
1               5

<210> SEQ ID NO 14
<211> LENGTH: 14
<212> TYPE: PRT
<213> ORGANISM: Artificial Sequence
<220> FEATURE:
<223> OTHER INFORMATION: Inhibitory peptide.

<400> SEQUENCE: 14

Asp Glu Glu Leu Gln Thr Glu Leu Tyr Glu Ile Lys His Gln
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Inhibitory peptide.

<400> SEQUENCE: 15

Asp Glu Glu Leu Gln Thr Glu Leu Tyr Glu Ile Lys
1               5                   10
```

```
<210> SEQ ID NO 16
<211> LENGTH: 11
<212> TYPE: PRT
<213> ORGANISM: Artificial Sequence
<220> FEATURE:
<223> OTHER INFORMATION: Inhibitory peptide.

<400> SEQUENCE: 16

Asp Glu Glu Leu Gln Thr Glu Leu Tyr Glu Ile
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Inhibitory peptide.

<400> SEQUENCE: 17

Asp Glu Glu Leu Gln Thr Glu Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Inhibitory peptide.

<400> SEQUENCE: 18

Thr Leu His Asp Phe Arg His Gln Ile Leu
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 19

Thr Leu His Asp Phe Arg His Gln Ile
1               5

<210> SEQ ID NO 20
<211> LENGTH: 8
<212> TYPE: PRT
<213> ORGANISM: Artificial Sequence
<220> FEATURE:
<223> OTHER INFORMATION: Inhibitory peptide.

<400> SEQUENCE: 20

Leu His Asp Phe Arg His Gln Ile
1               5

<210> SEQ ID NO 21
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 21

Glu Leu Tyr Glu Ile Lys His Gln Ile
1               5

<210> SEQ ID NO 22
```

```
<211> LENGTH: 8
<212> TYPE: PRT
<213> ORGANISM: Artificial Sequence
<220> FEATURE:
<223> OTHER INFORMATION: Inhibitory peptide.

<400> SEQUENCE: 22

Leu Tyr Glu Ile Lys His Gln Ile
1               5

<210> SEQ ID NO 23
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 23

Leu Lys Ile Glu Tyr His Gln Ile Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 24

Leu Arg Phe Asp His His Gln Ile Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 25

Leu His Glu Phe Lys His Gln Ile Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 26

Leu Phe Lys Leu Glu His Gln Ile Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 27

Leu His Asp Phe Arg Asp Gln Ile Leu
1               5

<210> SEQ ID NO 28
<211> LENGTH: 9
```

```
<212> TYPE: PRT
<213> ORGANISM: Artificial Sequence
<220> FEATURE:
<223> OTHER INFORMATION: Inhibitory peptide.

<400> SEQUENCE: 28

Leu His Asp Phe Arg Pro Gln Ile Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 29

Leu His Asp Phe Arg His Asn Ile Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 30

Leu His Asp Phe Arg His Ile Ile Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 31

Leu His Asp Phe Arg His Gln Leu Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Inhibitory peptide.

<400> SEQUENCE: 32

Leu His Asp Phe Arg His Gln Thr Leu
1               5

<210> SEQ ID NO 33
<211> LENGTH: 10
<212> TYPE: PRT
<213> ORGANISM: Homo sapiens

<400> SEQUENCE: 33

Glu Glu Glu Ala Lys Lys Leu Phe Pro Lys
1               5                   10
```

```
<210> SEQ ID NO 34
<211> LENGTH: 6
<212> TYPE: PRT
<213> ORGANISM: Artificial Sequence
<220> FEATURE:
<223> OTHER INFORMATION: Inhibitory peptide.

<400> SEQUENCE: 34

Ile Lys His Gln Ile Leu
1               5
```